(12) United States Patent
Leung

(10) Patent No.: US 7,491,514 B2
(45) Date of Patent: Feb. 17, 2009

(54) REDUCING THE IMMUNOGENICITY OF ANTI-CD20 ANTIBODIES BY FRAMEWORK PATCHING

(75) Inventor: Shawn Shui-on Leung, Kowloon (HK)

(73) Assignee: Skytech Technology Limited, Tortola (VG)

( * ) Notice: Subject to any disclaimer, the term of this patent is extended or adjusted under 35 U.S.C. 154(b) by 0 days.

(21) Appl. No.: 11/950,878

(22) Filed: Dec. 5, 2007

(65) Prior Publication Data

US 2008/0227957 A1    Sep. 18, 2008

Related U.S. Application Data

(62) Division of application No. 09/892,613, filed on Jun. 27, 2001, now Pat. No. 7,321,026.

(51) Int. Cl.
*C12P 21/04* (2006.01)
*A61K 39/395* (2006.01)
*C12P 21/08* (2006.01)
*C07K 16/00* (2006.01)

(52) U.S. Cl. ............... 435/69.6; 435/70.21; 424/133.1; 424/141.1; 424/144.1; 424/155.1; 530/388.1; 530/388.22; 530/388.73; 530/388.8

(58) Field of Classification Search .............. None
See application file for complete search history.

(56) References Cited

U.S. PATENT DOCUMENTS

| | | | |
|---|---|---|---|
| 4,704,362 | A | 11/1987 | Itakura et al. |
| 5,693,761 | A | 12/1997 | Queen et al. |
| 5,693,762 | A | 12/1997 | Queen et al. |
| 5,789,554 | A | 8/1998 | Leung et al. |
| 5,859,205 | A | 1/1999 | Adair et al. |
| 5,908,925 | A | 6/1999 | Cohen |
| 6,187,287 | B1 | 2/2001 | Leung et al. |
| 6,632,927 | B2 | 10/2003 | Adair et al. |

FOREIGN PATENT DOCUMENTS

| | | |
|---|---|---|
| DE | 4225853 | 2/1994 |
| EP | 0239400 | 9/1987 |
| WO | WO 9702671 | 5/1987 |
| WO | WO 9734632 | 9/1997 |
| WO | WO 9841641 | 9/1998 |
| WO | WO 9955369 | 11/1999 |

OTHER PUBLICATIONS

Johnson, Syd et al., Journal of Infectious Diseases, 1997; 176:1215-1224.
Adair, Fiona et al., BioPharm, Oct. 2000, pp. 42-46.
Amit, et al., Science, 1986; 233:747-753.
Benhar, et al., PNAS USA, 1994; 91(25) 12051-12055.
Bird, et al., Science, 1988; 242: 423-426.
Bruccoleri, et al., Nature, 1988; 335: 564-568.
Chatterjee, et al., Cancer Immunol. Immunother., 1994; 38: 75-82.
Chothia, et al., Nature, 1989; 342:877.
Chothia, et al., Science, 1986; 233: 755-758.
Chothia and Lesk, J. Mol. Biol., 1990; 215:175.
Coiffier, et al., Blood, 1998; 92: 1927-1932.
Co, Man Sung et al., PNAS USA, 1991; 88:2869-2973.
Daugherty, et al., Nucl. Acid Res., 1991; 19: 24712476.
Davis et al., J. Clin. Oncol., 1999; 17: 1851-1857.
Gillam and Smith, Gene, 1979; 8: 81-97.
Gura, Science, 1997; 278: 1041-1042.
Hamilton, et al., Journal of Infectious Diseases, 1997: 176:59-68.
Hunkapiller and Hood, Nature, 1986; 323:15-16.
Huston et al, PNAS USA, 1988; 85: 5879-5833.
Jones et al., Nature, 1986; 321: 522-525.
Kabat et al., Journal of Immunology, 1991; 147 (5): 1709-1719.
Leung et al., Mol. Immunol., 1995; 32: 1413-1427.
Levy et al., Biochemistry, 1989; 28:7168-7175.
Lewis et al., Immunology, 1993; 7: 110-118.
Li et al., Cell. Immunol., 1989; 118:85.
Mansfield et al., Blood, 1997; 90:2020-2026.
McLaughlin et al., J. Clin. Oncol., 1998; 16: 2825-2833.
Ohtomo et al., Mol. Immunol., 1995; 32: 407-416.
Padlan et al., Mol. Immunol., 1994: 31(3): 169-217.
Paul et al., *Fundamental Immunology*, Raven Press, New York, 1993: Chapter 8, p. 242.
Riechmann et al., Nature, 1988; 332: 323-327.
Roberts et al., Nature, 1987: 328:731-734.
Roguska et al., Protein Engineering, 1996: 9: 895-904.
Rosok et al., Journal of Biological Chemistry, 1996; 271(37): 22611-22618.
Rudikoff et al., PNAS, 1982; 79: 1979.
Rudikoff et al., PNAS USA, 1979; 79: 1979.
Sanger et al., PNAS, 1977; 74: 5463-5467.
Shan et al., Journal of Immunology, 1999'; 162: 6589-6595.
Shaw et al., J. Immunol., 1987; 138:4534-4538.
Shearman et al., Journal of Immunology, 1991; 147 (12): 4366-4373.
Singer et al., J. Immunol., 1993; 150: 2844-2857.
Tramamoto et al., J. Mol. Biol., 1990; 215: 175.

(Continued)

*Primary Examiner*—David J. Blanchard
(74) *Attorney, Agent, or Firm*—Chalin A. Smith; Smith Patent Consulting

(57) ABSTRACT

Framework (FR)-patching is a novel approach to modify immunoglobulin for reducing potential immunogenicity without significant alterations in specificity and affinity. Unlike previous described methods of humanization, which graft CDRs from a donor onto the frameworks of a single acceptor immunoglobulin, we patch segments of framework (FR1, FR2, FR3, and FR4), or FRs, to replace the corresponding FRs of the parent immunoglobulin. Free assortment of these FRs from different immunoglobulins and from different species can be mixed and matched into forming the final immunoglobulin chain. A set of criteria in the choice of these FRs to minimize or eliminate the need to reintroduce framework amino acids from the parent immunoglobulin for patching is described. The approach gives greater flexibility in the choice of framework sequences, minimizes the need to include parent framework amino acids, and, most importantly, reduces the chances of creating new T- and B-cell epitopes in the resultant immunoglobulin.

2 Claims, 12 Drawing Sheets

OTHER PUBLICATIONS

Figure 4:
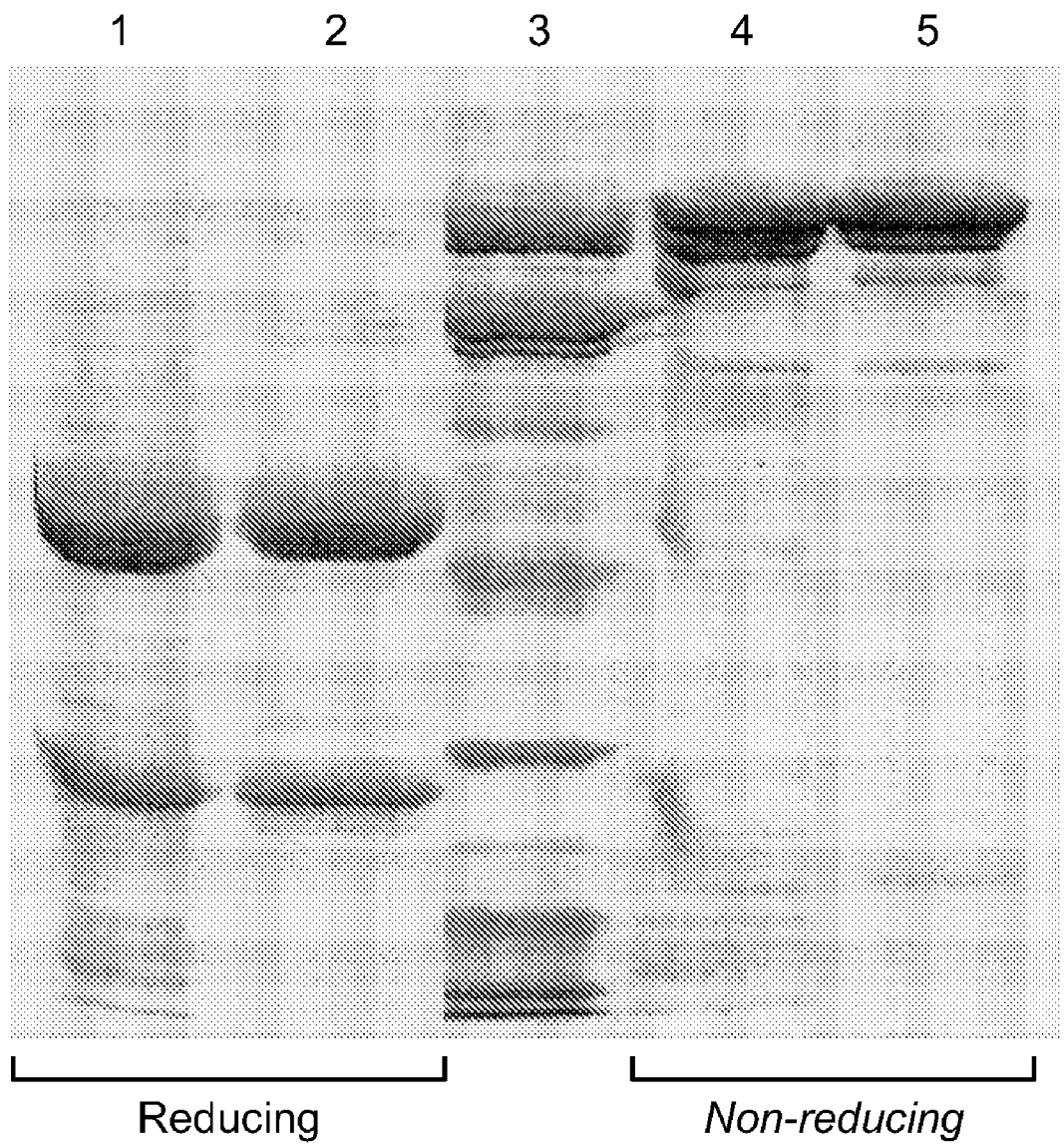

Verhoyen et al., Science, 1988; 85: 5879-5833.
Wu et al., Molecular Immunology, 1992; 29 (9): 1141-1146.
Wu et al., Applied Biochem and Biotech, 1994: 47: 107-118.
Zhengxing, et al., Clinical Cancer Research, 1999; vol. 5 (Suppl.):3095s-3100s.
International Search Report (Sep. 19, 2002), Written Opinion (Jan. 16, 2003), and Preliminary Examination Report (Dec. 19, 2003) for International Application No. PCT/US02/18512, filed Jun. 10, 2002, to Shawn Shui-on Leung.
Supplemental European Search Report from the European Patent Office (Jan. 30, 2007) for European Patent Application No. EP 02734771, filed Jan. 26, 2004, to Shawn Shiu-on Leung.
Complaint for Declaratory Judgment and Permanent Injunction (Including Exhibits A-G), Motion for Special Process Servers, Order Appointing Special Process Servers from Civil Action No. 2471-N. Oct. 12, 2006.
Supplemental Information Pursuant to Rule 3(a) of the Rules of the Court of Chancery, Oct. 12, 2006.

RFB4 VH sequence

E V Q L V E S G G G L V K P G G S L K L S C A A S G F A F S
‎[I Y D M S]‎ W V R Q T P E K R L E W V A ‎[Y I S S G G G T
T Y Y P D T V K G]‎ R F T I S R D N A K N T L Y L Q M S S L
K S E D T A M Y Y C A R ‎[H S G Y G S S Y G V L F A Y]‎ W G
Q G T L V T V S A

FIG.1A

RFB4 VL sequence

D I Q M T Q T T S S L S A S L G D R V T I S C ‎[R A S Q D I
S N Y L N]‎ W Y Q Q K P D G T V K L L I Y ‎[Y T S I L H S]‎
G V P S R F S G S G S G T D Y S L T I S N L E Q E D F A T Y
F C ‎[Q Q G N T L P W T]‎ F G G G T K L E I K

FIG.1B

```
VH
  |------------------------- FR1 -----------------------------|
     E V Q L V E S G G G L V K P G G S L K L S C A A S G F A F S
(EIK) E V Q L V E S G G G L V - P G G S L R L S C A T T G F A F S
(RF)  Q V Q L V E S G G G V V Q P G R S L R L S C A A S G F S F S
(WAS) E V Q L L E S G G G L V Q P G G S L R L S C A A S G F S F S

|---------- FR2 -----------|
    [I Y D M S]  W V R Q T P E K R L E W V A   [Y I S S G G G T]
        (WAS)   W V R Q A P G K G L E W V A

|------------------ FR3 ------------------|
    [T Y Y P D T V K G]  R F T I S R D N A K N T L Y L Q M S S L
           (GAL)         R F T I S R D N A K N S L Y L Q M N S L

|---------- FR3 ----------|                                 |----
    K S E D T A M Y Y C A R   [H S G Y G S S Y G V L F A Y]   W G
    R V E D T A L Y Y C A R                      (DOB)        W G

|-------- FR4 -------|
    Q G T L V T V S A
    Q G T L V T V S T
```

FIG.2A

VL
```
       |-------------------- FR1 --------------------|
       D I Q M T Q T T S S L S A S L G D R V T I S C   [R A S Q D I]
(JOH)  D I Q M T Q S P S S L S A S V G D R V T I S C
```

```
                  |------------ FR2 ------------|
     [S N Y L N]  W Y Q Q K P D G T V K L L I Y    [Y T S I L H S]
                  W Y Q Q K P G K A P K L L I Y
        (Vd'CL)
```

```
       |---------------------------- FR3 ----------------------------|
       G V P S R F S G S G S G T D Y S L T I S N L E Q E D F A T Y
(WES)  G V P S R F S G S G S G T E F T L T I S S L Q P E D F A T Y
```

1. cRFB4 (reducing)
2. hpRFB4 (reducing)
3. Size Marker
4. cRFB4 (non-reducing)
5. hpRFB4 (non-reducing)

|------------ FR2 ------------|
         [S Y N M H]   W V K Q T P G Q G L E W I G   [A I Y P G N G D]
          (NEWM)       W V R Q P P G R G L E W I G

|------------------ FR3 ------------------|
         [T S Y N Q K F K G]   K A T L T A D K S S S T A Y M Q L S S L
              (783C'CL)        R V T I T A D K S T S T A Y M E L S S L
               (58'CL)         R A T I S V D T S K N Q F S L N L S S V

|---------- FR3 ----------|                                    |------
 T S E D S A V Y Y C A R       [S H Y G S N Y V D Y F D Y]   W G Q
 R S E D T A V Y Y C A R                    (4G12'CL)        W G Q
 T A A D T A V Y C C A R

---- FR4 ----------|
G T T L T V S S D
G T T V T V S S -
```

FIG.8A

```
VL
         |-------------------- FR1 --------------------|
         Q I V L S Q S P A I L S A S P G E K V T M T C   R A S S S L
(BJ19)   D I Q L T Q S P S S L S A S V G D R V T I T C
(6NIG)   N L M L I Q P P S - V S E S P G K T V T M T C

|------------- FR2 -------------|                |--
         S F M H      W Y Q Q K P G S S P K P W I Y      A T S N L A S   G
         (MOT)        W Y Q Q K P G Q A P V P V I Y            (WES)     G
                                                               (AND#)    G
                                                               (RZ)      G
                                                               (NOT)     G

----------------------------- FR3 -----------------------------
         V P A R F S G S G S G T S Y S L T I S R V E A E D A A T Y F
(WES)    V P S R F S G S G S G T E F T L T I S S L Q P E D F A T Y F
(AND#)   V P S R F S G S G S G T D F T L T I T S L Q P E D F A A Y F
(RZ)     V P S R F T G S G S G T D F F L T I S S L R P E D V A T Y F
(NOT)    V P A R F S G Y N S G N S A F L T I N R V E A G D E A D Y F

--|             |---------- FR4 ----------|
         C   H Q W S S N P L T    F G A G T K L E L K R
         C             (LS1'CL)   F G G G T K V E I K R
         C             (NI)       F G V G S K V E S K R
         C             (NIG-58)   F G A G T K L T V L R
         C
```

VH
QVQLVASGAEVNKPGASVKVSCKASGYTFT
SYNMH WVRQPPGRGLEWIG AIYPGNGD
TSYNQKFKG RVTITADKSTSTAYMELSSL
RSEDTAVYYCAR SHYGSNYVDYFDY WGQ
GTTVTVSS-

FIG. 10A

VL
DIQLTQSPSSLSASVGDRVTITC RASSSL
SFMH WYQQKPGQAPVPVIY ATSNLAS G
VPSRFSGSGSGTEFTLTISSLQPEDFATYF
C HQWSSNPLT FGAGTKLTVLR

FIG. 10B

… # REDUCING THE IMMUNOGENICITY OF ANTI-CD20 ANTIBODIES BY FRAMEWORK PATCHING

This application is a divisional of U.S. application Ser. No. 09/892,613, filed on Jun. 27, 2001, now U.S. Pat. 7,321,026, the contents of which are hereby incorporated by reference into this application.

Throughout this application, various references are referred to within parenthesis. Disclosures of these publications in their entireties are hereby incorporated by reference into this application to more fully describe the state of the art to which this invention pertains.

FIELD OF THE INVENTION

The present invention relates to novel methods in re-engineering, or reshaping antibodies with clinical indications (both therapeutic and diagnostic). The method combines the use of recombinant technology and, stepwise and systemic approaches in re-designing antibody sequences. The invention particularly provides for antibodies which are modified to be less immunogenic than the unmodified counterpart when used in vivo.

BACKGROUND OF THE INVENTION

Monoclonal antibodies (Mabs) have become the most successful protein drugs being used for the treatment of a variety of diseases, including cancers, transplantation, viral infection, etc. However, the concept of magic bullet took more than 25 years to realize, because there were problems associated with the use of monoclonal antibodies. One of the main problems stems from the original source of most monoclonal antibodies, which are of rodent and murine origin. Repeated injections of these foreign proteins into human would inevitably result in the elicitation of host immune responses against the antibodies: the so-called human anti-mouse antibody (HAMA) responses. Although earlier attempts to use the techniques of molecular engineering to construct chimeric antibodies (for example, mouse variable regions joined to human constant regions) were somewhat effective in mitigating HAMA responses, there remains a large stretch of murine variable sequences constituting ⅓ of the total antibody sequence that could be sufficiently immunogenic in eliciting human anti-chimeric antibody (HACA) responses. A more advanced improvement in antibody engineering has recently been utilized to generate humanized antibodies in which the complementarity determining regions (CDR's) from a donor mouse or rat immunoglobulin are grafted onto human framework regions (for example, EPO Publication No. 0239400, incorporated herein by reference). The process is called "humanization", or "CDR-grafting". The original concept of humanization describes the direct grafting of CDR's onto human frameworks, reducing the non-human sequences to less than 5%, and thereby the HAMA and HACA responses. However, direct replacement of framework sequences without further modifications can result in the loss of affinity for the antigen, sometimes as much as 10-fold or more (Jones et al., Nature, 321:522-525, 1986; Verhoyen et al., Science, 239:1534-1536, 1988). To maintain the affinity of the CDR-grafted or humanized antibody, substitutions of a human framework amino acid of the acceptor immunoglobulin with the corresponding amino acid from a donor immunoglobulin at selected positions will be required. The positions where the substitution takes place are determined by a set of published criteria (U.S. Pat. No. 5,85,089; U.S. Pat. No. 5,693,762; U.S. Pat. No. 5,693,761; incorporated herein by reference). However, the presence of murine amino acids within stretches of human framework sequences can be immunogenic in the generation of new T- and B-cell epitopes. Moreover, the identification of the proper framework amino acids to be replaced can sometimes be difficult, further reducing the chances of success in humanization without significant impacts on the specificity and affinity of the humanized antibody.

New and improved means for producing re-engineered immunoglobulin with reduced or eliminated immunogenicity while maintaining the specificity and affinity of the parent antibody are therefore needed. Preferably, the re-engineered immunoglobulin should contain no FR amino acid substitutions from the parent antibody, which can be a likely source of immunogenic epitopes for T- or B-cells. However, the approach also offers flexibility in the sequence design where few murine residues or a stretch of murine sequences can be included in the final design, with the ultimate goal of reducing immunogenicity while maintaining specificity and affinity of the resultant antibody for human uses. The present invention describes the methods and approaches in fulfilling these goals.

SUMMARY OF THE INVENTION

The present invention relates to novel methods for re-engineering immunoglobulin chains having generally one or more complementarity determining regions (CDR's) from a donor immunoglobulin and portions of framework sequences from one or more human, or primate immunoglobulins. The preferred methods comprise first dividing the framework sequences from immunoglobulins of all species into compartmentalized subregions of FR1, FR2, FR3, and FR4, according to the Kabat Database (Kabat et al. Sequences of proteins of immunological interest. Maryland: US Department of Health and Human Services, NIH, 1991), and comparing the individual FR's, instead of the whole framework, in the variable region amino acid sequence subregions of the parent immunoglobulin to corresponding sequences in a collection of human, or primate immunoglobulin chains, and selecting the appropriate human or primate FR's with the highest degree of homology to replace the original FR's of the parent immunoglobulin (framework- or FR-patching). The human FR's can be selected from more than one human or primate immunoglobulin sequences. A collection of human or primate immunoglobulin sequences can be obtained from different databases (for example, Kabat database, National Biomedical Research Foundation Protein Identification Resource, Brookhaven Protein Data Bank, internet, etc.). The individual FR sequences selected from human or primate immunoglobulins will typically have more than 60% homology to the corresponding parent FR sequences. Although high overall homology will be an important criteria for selecting the FR's for patching, lesser homology FR's will be used if the homology of sequences directly flanking the CDR's or at loop positions where contact(s) with the antigen binding site is (are) determined experimentally or predicted via computer modeling. The parent immunoglobulin whose FR's are to be patched may be either a heavy chain or light chain. A patched light and heavy chain can be used to form a complete FR-patched immunoglobulin or antibody, having two light/heavy chain pairs, with or without partial or full-length human constant regions.

The individual FR's chosen for patching a parent immunoglobulin chain (applies to both heavy and light chains) should:

(1) preferably have amino acid sequences immediately adjacent to the CDR's identical to that of the parent immunoglobulin chain;
(2) have amino acid sequences immediately adjacent to the CDR's conservatively similar in structure to, if not completely identical to, that of the parent immunoglobulin chain;
(3) preferably have identical amino acid at corresponding FR position of the parent immunoglobulin predicted to be within about 3Å of the CDR's (or the effective antigen-binding site) in a three-dimensional immunoglobulin model and capable of interacting with the antigen or with the CDR's of the parent or FR-patched immunoglobulin;
(4) have amino acid conservatively similar in structure to amino acid at corresponding FR position of the parent immunoglobluin predicted to be within about 3Å of the CDR's (or the effective antigen-binding site) in a three-dimensional immunoglobulin model and capable of interacting with the antigen or with the CDR's of the parent or FR-patched immunoglobulin.

Each of the heavy and light chains of the FR-patched immunoglobulin will typically comprise FR's sourced from one or more human or primate immunoglobulins according to any one or all of the selection criteria. The FR-patched heavy and light chains of the present invention, when combined into an intact antibody, antibody fragment, or antibody-based derivatives (for example single-chain antibody, diabodies, etc.), will be substantially non-immunogenic in humans and retain substantially the same affinity and properties (for example internalization upon binding) as the parent immunoglobulin to the antigen. These affinity levels should vary within the range of 4-fold, and preferably within about 2 fold of the parent immunoglobulin's original affinity to the antigen.

Similar principles apply to re-engineer, or patch, parent immunoglobulins of one species with the FR's from a different species. People skilled in the art of protein and/or molecular engineering will be able to adopt the design and principle of the present invention to produce FR-patched immunoglobulins, or derivatives thereof. Once designed, there exist a variety of techniques in constructing the FR-patched immunoglobulin sequence, for example, by site-directed mutagenesis, and gene-synthesis. The assembled FR-patched sequences will be subcloned into expression vectors containing the appropriate immunoglobulin constant heavy and light chains for transfection in producer cell lines. Different cell systems can be used for the production of the FR-patched immunoglobulins, including bacterial, yeast, insect, and mammalian cells.

Alternatively, the immunoglobulins can be produced in the milks of transgenic or transomatic animals, or as stored proteins in transgenic plants. The present invention offers an improved and novel methods, that are relatively easy (no need to identify important FR amino acid interacting with the CDR's) and highly flexible (freedom to match, and change if necessary, individual FR's) in generating immunoglobulins with reduced or eliminated immunogenicities without sacrificing binding affinity and the likelihood of introducing new T- and B-cell epitopes resulting from the introduction of parent immunoglobulin's framework amino acids into the human FR's. The FR-patched antibodies will be suitable for human use in treating a variety of disease, either used singly or repeatedly, at low (less than 10 mg/m$^2$) or high (more than 100 mg/m$^2$) doses, in naked forms or as fusion or chemical conjugates, used alone, or in conjunction with other immunoglobulins or treatment modalities.

DETAILED DESCRIPTION OF THE FIGURES

FIG. 1A and FIG. 1B. Amino acid sequences (single-letter code) of the heavy chain (VH)(A) and light chain (VL)(B) variable regions of the murine anti-CD22 antibody, RFB4. CDR's are boxed. (SEQ ID NO. 33 and 34)

FIG. 2A and FIG. 2B. Comparison of the compartmentalized framework sequences (FR's) of the heavy chain (A) and light chain (B) variable regions of RFB4, with the different human FR's of the highest homology. The FR1, FR2, FR3, and FR4 are indicated. The CDR's are boxed. The bracketed italic next on the left of the FR sequence indicates the source of the human FR. Amino acids in the human FR's that are different from that of the corresponding murine FR's are in bold. (SEQ ID NO. 35-46)

FIG. 3A and FIG. 3B. The final designed sequences (single-letter code) of the heavy chain (A) and light chain (B) variable regions of the FR-patched antibody, hpRFB4. CDR's are boxed. Amino acids in the human FR's that are different from that of the original murine FR's are in bold. (SEQ ID NO. 47-48)

FIG. 4. Predicted SDS-PAGE analysis of purified cRFB4 and hpRFB4 under both reducing and non-reducing conditions.

Figure 5:
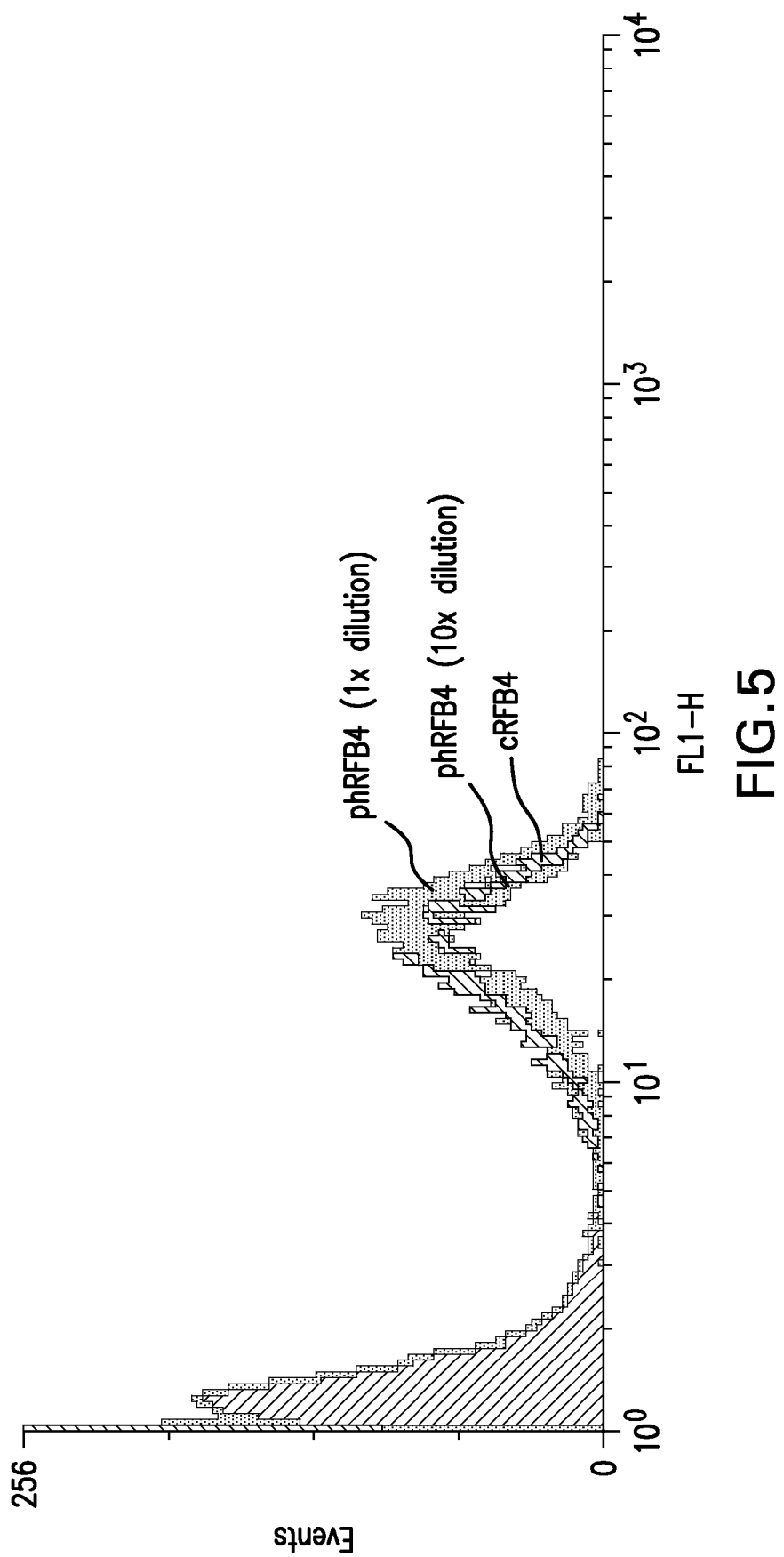

FIG. 5. Predicted flow cytometry analyses on the binding specificity and affinity of cRFB4 and hpRFB4 on Raji cells.

Figure 6:
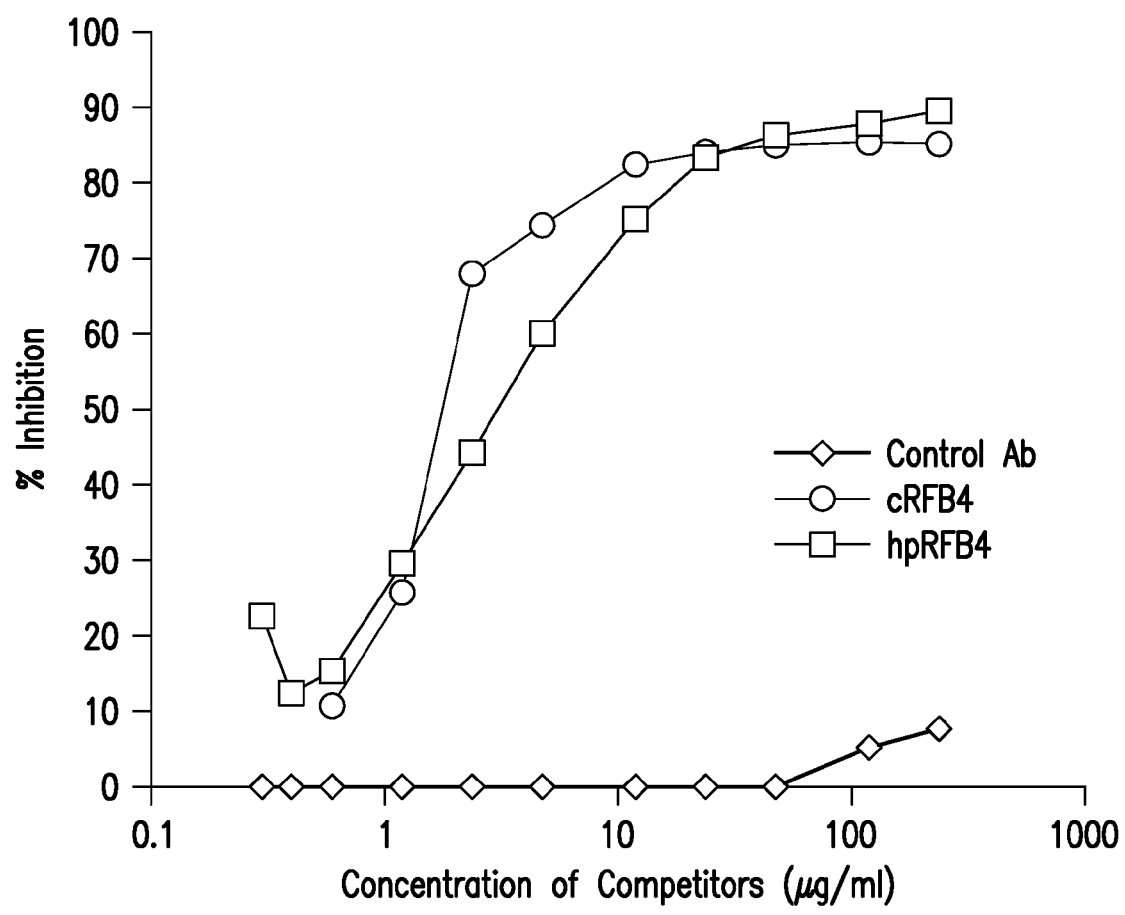

FIG. 6. Predicted competition binding assay comparing the binding affinity between cRFB4 and hpRFB4. An irrelevant antibody was used as a control.

FIG. 7A and FIG. 7B. Amino acid sequences (single-letter code) of the heavy chain (A) and light chain (B) variable regions of the murine anti-CD20 antibody, 1F5. CDR's are boxed. (SEQ ID NO. 49-50)

FIG. 8A and FIG. 8B. Comparison of the compartmentalized framework sequences (FR's) of the heavy chain (A) and light chain (B) variable regions of 1F5 with the different human FR's of the highest homology. The FR1, FR2, FR3, and FR4 are indicated. The CDR's are boxed. The bracketed italic next on the left of the FR sequence indicates the source of the human FR. Amino acids in the human FR's that are different from that of the corresponding murine FR's are in bold. (SEQ ID NO. 51-67)

FIG. 9A and FIG. 9B. The final designed sequences (single-letter code) of the heavy chain (A) and light chain (B) variable regions of the FR-patched antibody, hp1F5. CDR's are boxed. Amino acids in the human FR's that are different from that of the original murine FR's are in bold. Murine FR's not replaced by human sequences are underlined. (SEQ ID NO. 68-69)

FIG. 10. Amino acid sequence of an alternative design of FR-patched variable regions for 1F5 (Alternative Design). CDR's are boxed. Human framework amino acids that differ from that of the corresponding murine frameworks are in bold. A. The heavy chain variable region (VH) amino acid sequence of FR-patched 1F5 (Alternative Design); (SEQ ID NO. 70) B. The light chain variable region (VL) amino acid sequence of FR-patched 1F5 (Alternative Design). (SEQ ID NO. 71)

DETAILED DESCRIPTION OF THE INVENTION

The present invention aims to establish novel approaches in the design of immunoglobulin with high degree of homology to human or primate sequences through a process named "framework (FR) patching". The FR-patched immunoglobulin (patched immunoglobulin thereafter) will have substantially reduced, or eliminated immunogenicity when used in human, and carry most or all of the characteristics of a human immunoglobulin such as the ability to target specific antigens, and effector functions (for example, complement fixation, ADCC, etc.), while maintaining the specificity and affinity of the parent immunoglobulin against a specific antigen. The patched immunoglobulin will comprise a heavy and light chain, of which, the respective variable region will contain sequences representing FR1, CDR1, FR2, CDR2, FR3, CDR3, and FR4, according to Kabat's classification (Kabat et al., op. cit.). At least one of the four FR's of each parent immunoglobulin chain containing one or more complementary determining regions (CDR's) will be replaced, or "patched" with, a corresponding human or primate FR. When two or more FR's of the parent immunoglobulin chain are to be replaced, they can be patched with corresponding FR's either from the same human or primate immunoglobulin, or from different human or primate immunoglobulin within the same subgroup or in different subgroups, or from a combination of human and primate immunoglobulins. The patched immunoglobulins will be expressed in appropriate host system for large-scale production at typical pharmaceutical margins, and used in humans at appropriate formats or combinations to treat or detect a wide range of human diseases.

To ensure a better understanding of the present invention, several definitions are set forth. As used herein, an "immunoglobulin" refers to a protein consisting of one or more polypeptides substantially encoded by immunoglobulin genes. A typical immunoglobulin protein contains two heavy chains paired with two light chains. A full-length immunoglobulin heavy chain is about 50 kD in size (approximately 446 amino acids in length), and is encoded by a heavy chain variable region gene (about 116 amino acids) and a constant region gene. There are different constant region genes encoding heavy chain constant region of different isotypes such as alpha, gamma (IgG1, IgG2, IgG3, IgG4), delta, epsilon, and mu sequences. A full-length immunoglobulin light chain is about 25 Kd in size (approximately 214 amino acids in length), and is encoded by a light chain variable region gene (about 110 amino acids) and a kappa or lambda constant region gene. Naturally occurring immunoglobulin is known as antibody, usually in the form of a tetramer consisting of two identical pairs of immunoglobulin chains, each pair having one light and one heavy chain. In each pair, the light and heavy chain variable regions are together responsible for binding to an antigen, and the constant regions are responsible for the effector functions typical of an antibody.

Immunoglobulin may be in different forms, either naturally occurring, chemically modified, or genetically-engineered, such as Fv (Huston et al., Proc. Natl. Acad. Sci. USA. 85:5879-5833; Bird et al., Science 242:423-426, 1988), diabodies, mini-antibodies, Fab, Fab', F(ab')$_2$, bifunctional hybrid antibodies (Lanzavecchia et al., Eur. J. Immunol. 17:105, 1987) (See, generally, Hood et al., "Immunology", Benjamin, NY, 2$^{nd}$ ed. 1984; Hunkapiller and Hood, Nature 323:15-16, 1986).

The variable region of both the heavy and light chain is divided into segments comprising four framework sub-regions (FR1, FR2, FR3, and FR4), interrupted by three stretches of hypervariable sequences, or the complementary determining regions (CDR's), as defined in Kabat's database (Kabat et al., op. cit.), with the CDR1 positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FR's represents two or more of the four sub-regions constituting a framework region. The sequences of the framework regions of different light or heavy chains are relatively conserved within a species. The framework region of an antibody is the combined framework regions of the constituent light and heavy chains and serves to position and align the CDR's. The CDR's are primarily responsible for forming the binding site of an antibody conferring binding specificity and affinity to an epitope of an antigen.

Parent antibody is an antibody of a particular species, for example, murine, which is to be re-engineered, re-shaped, or in this invention, FR-patched into a form, sequence, or structure, appropriate for use in a different species, for example, human, with reduced or minimized immunogenicity.

Chimeric antibodies are antibodies whose variable regions are linked, without significant sequence modifications from the parent V-region sequences, to the corresponding heavy and light chain constant regions of a different species. Construction of a chimeric antibody is usually accomplished by ligating the DNA sequences encoding the variable regions to the DNA sequences encoding the corresponding constant chains. The most common types of chimeric antibodies are those containing murine variable regions and human constant regions. In this case, the expressed hybrid molecule will have the binding specificity and affinity of the parent murine antibody, and the effector functions of a human antibody. Most importantly, $\frac{2}{3}$ of the amino acids of the recombinant protein are of human origin, a reduced or insignificant immunogenicity is therefore expected when used in human, as in the case of the therapeutic chimeric antibody C2B8 (or RITUXIMAB) (Davis et al., J. Clin. Oncol. 17:1851-1857, 1999; Coiffier et al., Blood 92:1927-1932, 1998; McLaughlin et al., J. Clin. Oncol. 16:2825-2833, 1998).

A "humanized" immunoglobulin is generally accepted as an immunoglobulin comprising a human framework region and one or more CDR's from a non-human immunoglobulin (Jones et al., op. cit; Verhoeyen et al., op. cit; Riechmann et al., op. cit.). The non-human immunoglobulin providing the CDR's is called the "donor" and the human immunoglobulin providing the framework is called the "acceptor". Usually, as has been used and referred to by others, an acceptor is derived from a single human immunoglobulin species. To maintain the affinity of the "humanized" immunoglobulin, donor amino acid residues may have to be incorporated in the framework region of the acceptor immunoglobulin. There is a set of criteria for selecting a limited number of amino acids within the acceptor immunoglobulin for conversion into donor sequences, as published in a series of publications (U.S. Pat. No. 5,85,089; U.S. Pat. No. 5,693,762; U.S. Pat. No. 5,693,761; incorporated herein by reference). The humanized immunoglobulins may or may not contain constant regions. A humanized heavy chain immunoglobulin is a humanized immunoglobulin comprising a corresponding human heavy chain constant region, and a humanized light chain immunoglobulin is a humanized immunoglobulin comprising a corresponding human light chain constant region. A humanized antibody is an antibody comprising a humanized light chain and a humanized heavy chain immunoglobulin.

A successful humanized antibody will have to have the following characteristics:
(1) significantly reduced, and preferably eliminated, immunogenicity resulting from the humanized sequences, allowing multiple injection of the humanized antibody for human uses;
(2) minimally perturbed immunoreactivity including specificity and affinity (within 3-fold) against the original antigen;

(3) capable of inducing human effector functions such as complement fixation, complement-mediated cytotoxicity, antibody-dependent cell cytotoxicity, etc.

Direct grafting of donor CDR's onto human acceptor framework without further sequence modifications, will likely result in substantial loss of antigen affinity. Although the introduction of selected donor amino acids to acceptor framework regions will somehow rectify the problem, and most of the time, improve affinity, however, the approach is tedious, requiring sometimes the assistance of computer modeling in identifying the appropriate framework amino acid to mutate, and lack flexibility in the choice of acceptor human frameworks in an all-or-none mode. Most importantly, it is likely to introduce potential new immunogenic epitopes by retaining parent "donor" residues in the human "acceptor" framework.

The present invention addresses these problems and creates a novel approach with increased flexibility and simplicity in generating a FR-patched antibody that is not immunogenic or is low in immunogenicity, yet having retained most or all of the original affinity against a specific antigen, as in the parent antibody. Since most of the immune responses against a chimeric or humanized immunoglobulin will be directed against epitopes in the variable regions, without intending to be bound by theory, the principle by which the invention comes about will be illustrated by, but not limited to, using the variable region as the example.

There exist at least two kinds of epitopes contributing to the immunogenicity against a protein. The so-called "T cell epitopes" are short peptide sequences released during the degradation of proteins within cells and subsequently presented by molecules of the major histocompatability complexes (MHC) in order to trigger the activation of T cells. For peptides presented by MHC class II, such activation of T cells can then give rise to an antibody response by direct stimulation of B cells to produce such antibodies. A detailed analysis of the structure of a humanized variable region reveals the unavoidable existence of stretches of potentially immunogenic CDR's. These CDR's physically and functionally compartmentalize the rest of the framework sequences into four sub-regions, namely, the FR1, FR2, FR3, and FR4 (Kabat et al., op. cit.). Since T cell epitopes are linear continuous short peptides, the presence or absence of such epitopes in each FR compartments should have no correlation to each other, whether the different FR's are derived from the same or different frameworks. The introduction of donor framework residues to the acceptor framework region using the humanization approach of Queen et al. (U.S. Pat. No. 5,85,089; U.S. Pat. No. 5,693,762; U.S. Pat. No. 5,693,761; incorporated herein by reference) will have the possibility of generating new, immunogenic T cell epitopes, resulting in the elicitation of immune responses against the humanized antibody, particularly antibody responses against the idiotypic region formed by the donor CDR loops. It is uncommon to have between 3 to 7 donor amino acids incorporated into each humanized immunoglobulin chain, greatly increasing the chances of emergency for new T cell epitopes.

Similarly, these donor-derived residues embedded within the human framework can form new immunogenic B-cell epitopes recognizable by antibodies. While it is well-established that re-introduction of donor residues to the acceptor framework is important in maintaining the original antigen affinity of the humanized immunoglobulin, ideally, it would be preferable if humanization can be accomplished by direct grafting of donor CDR's onto acceptor framework without additional modification and loss of affinity.

The present invention provides a new approach in reducing or eliminating the immunogenicity of immunoglobulins whose affinity against the specific antigen is maintained within three fold of its original level. The approach is flexible, versatile, simple, and does not usually require sophisticated computer modeling analysis (although it does not preclude its being used). It deals with the problem of reciprocal relation between reducing immunogenicity and maintaining affinity in humanizing an antibody with the previous and available methodologies. Using an immunoglobulin variable region as example, a set of criteria and principles will be followed in FR-patching the sequence. The criteria may be used singly, or when necessary in combination, to achieve reduced or eliminated immunogenicity, and the desired affinity or other characteristics.

In humanizing an immunoglobulin variable region by FR-patching, the parent immunoglobulin amino acid sequences are compartmentalized into FR1, CDR1, FR2, CDR2, FR3, CDR3, and FR4 according to the classification of Kabat et al. (opt. cit.). Each of the compartmentalized FR's will be dealt with separately and used to align with the corresponding FR segments found in all databases, available either in the public domain, commercial entities, or private possession (for example the Kabat database, opt. cit.; the National Biomedical Research Foundation Protein Identification Resource). An immunoglobulin can be patched with FR's from more than one immunoglobulin sources. Preferably, human FR segments with the highest degree of homology (>60%) to the corresponding parent FR's will be used. However, amino acids in the FR's adjacent to one or more of the 3 CDR's in the primary sequence of the immunoglobulin chain may interact directly with the antigen (Amit et al., Science, 233:747-753, 1986, which is incorporated herein by reference) and selecting these amino acids identical to the human FR's with lesser homology will be used according to the criteria set forth below.

A human FR1 will be used when it has the highest homology to the parent FR1, preferably 100%, at three or more amino acids immediately adjacent to CDR1.

A human FR2 will be used when it has the highest homology to the parent FR2, preferably 100%, at three or more amino acids at both ends immediately adjacent to the flanking CDR1 and CDR2.

A human FR3 will be used when it has the highest homology to the parent FR3, preferably 100%, at three or more amino acids at both ends immediately adjacent to the flanking CDR2 and CDR3.

A human FR4 will be used when it has the highest homology to the parent FR4, preferably 100%, at three or more amino acids immediately adjacent to CDR3.

In case human FR's with 100% homology at three or more amino acids adjacent to the CDRs cannot be identified, FR's with the closest homology at these positions containing conservatively similar amino acids, such as, gly, ala; val, ile, leu; asp, glu; asn, gln; ser, thr; lys, arg; and phe, tyr; will be selected.

Preferably, human FR's whose amino acids at positions known to be close to, or have interactions with the CDR's/antigen binding site (Chothia and Lesk, J. Mol. Biol. 196:901, 1987; Chothia et al., Nature 342:877, 1989, and Tramontano et al., J. Mol. Biol. 215:175, 1990, all of which are incorporated herein by reference), either based on computer modeling (see Levy et al., Biochemistry 28:7168-7175, 1989; Bruccoleri et al., Nature 335:564-568, 1988; Chothia et al., Science 233:755-758, 1986, all of which are incorporated herein by reference), crystal structure, published information, or prior experience, which are identical, or conservatively similar to that of the parent FR's will be selected.

FR-patching does not preclude the introduction of parent amino acids at corresponding positions of a patched FR where necessary, or the inclusion of FR's in the immunoglobulin from different species such as different primates, murine, etc, when available databases fail to produce a satisfactory FR that meet the above criteria. The primary goal is to produce antibodies with reduced, preferably, eliminated immunogenicity without substantial loss of affinity. The approach increases the chances of success in this regard, with significant improvements over other methods in terms of flexibility, simplicity, and ease of operation.

FR-patched antibodies carrying human constant sequences will be able to induce human immune effector functions such as complement-mediated cytotoxicity (CM) or anti-body-dependent cellular cytotoxicity (ADCC), upon binding to the target antigens. Moreover, when injected in human for therapeutic or diagnostic purposes, antibodies patched with human FR's are expected to be non-immunogenic, i.e., will not elicit antibody responses against the injected protein, allowing for multiple injections into human patients if necessary for achieving maximum clinical benefits. Non-human antibodies have been reported to have significantly shorter circulation half-lives than that of human antibodies (Shaw et al., J Immunol. 138:4534-4538, 1987). The patched antibodies, carrying mostly human sequences, will presumably have an extended half-life reminiscent to naturally occurring human antibodies.

In the construction of a FR-patched immunoglobulin, sequence design for the variable regions of the immunoglobulin will be done using the criteria and principles illustrated above. The designed FR-patched variable region sequence will be assembled using a variety of standard recombinant techniques well known to those skilled in the art. Preferably, the designed sequence, usually of a size of about 350 base pairs, will be gene-synthesized (Leung et al., Molecular Immunol. 32:1413-1427, 1995; Daugherty et al., Nucl. Acid Res. 19:2471-2476; DeMartino et al., Antibody Immunoconj. Radiopharmaceut. 4:829, 1991; Jones et al., op. cit., all of which are incorporated herein by reference), or the individual FR's can be introduced to replace the parent FR's by methods of site- or oligonucleotide-directed mutagenesis (Gillman and Smith, Gene 8:81-97, 1979; and Roberts et al., Nature 328:731-734; both of which are incorporated herein by reference).

The DNA segment encoding the FR-patched immunoglobulin will be joined to DNA sequences encoding the human heavy and light chain regions in DNA expression vectors suitable for bacterial propagation and expression in different host cells. There are a variety of DNA vectors suitable for expression in a variety of host cell systems. Appropriate DNA vectors can be chosen for the expression of the FR-patched immunoglobulins. Typically, a suitable expression control DNA sequence is linked operably to DNA segments encoding the immunoglobulin chains. Preferably, the expression control sequences will be eukaryotic promoter systems in vectors capable of transforming or transfecting eukaryotic host cells, but control sequences for prokaryotic hosts may also be used. The sequence encoding the FR-patched heavy and light immunoglobulin chains can be incorporated into one single DNA expression vector, or into separate heavy and light chain expression vectors. In the latter case, host cells will have to be simultaneously incorporated with both vectors in order to produce a FR-patched antibody with the properly paired heavy and light chain polypeptides. In general, a leader sequence allowing the transportation of the immunoglobulin polypeptide into the Golgi apparatus for later secretion is included at the N-terminal end of each immunoglobulin chain for expression in eukaryotic host cells. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments, single chain antibody (sFv), diabodies, or derivatives thereof, or other immunoglobulin forms may follow (see Beychok, Cells of Immunoglobulin Synthesis, Academic Press, NY, 1979, which is incorporated herein by reference).

It is a well-known fact that there are different human constant regions for the heavy and light chains. A particular isotype will have specific effector characteristics that can be chosen for use for different purposes. Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to the predetermined antigens, such as CD22 and CD20, for example, and produced by well known methods in any convenient mammalian source including, mice, rat, rabbits, or other vertebrate, capable of producing antibodies. Suitable source cells for the constant region and framework DNA and secretion, can be obtained from a number of sources such as the American Type Culture Collection ("Catalogue of Cell Lines and Hybridomas," sixth edition, 1988, Rockville, Md., USA, which is incorporated herein by reference).

DNA expression vectors containing the coding sequences for the FR-patched immunoglobulin chains operably linked to an expression control sequence (including promoter and enhancers) are typically replicable in the host organisms either as episomes or as an integral part of the host chromosomal DNA. Selectable markers such as tetracycline, neomycin, beta-lactamase, etc., are included in the vector to allow detection of cells transformed with the DNA vectors (see, for example, U.S. Pat. No. 4,704,362, which is incorporated herein by reference).

Bacterial hosts are suitable for propagating the DNA vectors as well as expressing the incorporated immunoglobulin DNA. For example, *E. coli* is the most commonly used prokaryotic host used for cloning the DNA sequence for the present invention. Other microbial hosts that are useful for the same purposes include, as examples, bacilli (for example *Bacillu subtilus*), and other enterobacteriaceae (for example *Salmonella, Serratia*), and various *Pseudomonas* species. Expression of cloned sequences in these hosts require the presence of expression control sequences compatible with the host cell (for example an origin of replication), and functional promoters to be included in the DNA vector. Example of well-known promoter system include, but not limited to, tryptophan (trp) promoter system, beta-lactamase promoter system, phage lambda promoter system, etc. These promoters are responsible for controlling expression, or transcription, of the functional gene sequence downstream of the promoter system, which contains, in addition to all necessary motifs, and optionally with an operator sequence, ribosome binding site sequences and the like, necessary for transcription initiation and translation.

Similarly, other microbes, such as yeast, may also be used for expression. For example, a preferred host will be *Saccharomyces*, which is a suitable host for expression vectors containing the appropriate expression control elements, such as promoters, including 3-phosphoglycerate kinase or other glycolytic enzymes, and an origin of replication, termination sequences and the like as desired.

Eukaryotic host cells of invertebrate origin can be used. For example, insect cells, such as hi-5, SF9, SF21. Appropriate expression vectors containing convenient cloning sites, promoters, termination sequences, etc., that are important for high-level expression in the host cells are available commercially (Invitrogen, San Diego, Calif.).

Preferably, mammalian tissue cell culture may be used to express and produce the polypeptides of the present invention (see, Winnacker, "From Genes to Clones," VCH Publisher, NY, N.Y., 1987, which is incorporated herein by reference). The most commonly used mammalian host cells are Chinese Hamster Ovary (CHO) cell lines, various COS cell lines, HeLa cells, and myeloma cell lines such as SP2/0 cell lines, NS0 cell lines, YB2/0 cell lines, etc, and transformed B-cells or hybridomas. These cell lines are capable of conferring the right glycosylation at appropriate site such as amino acid 297 at the heavy chain CH2 domain, and secreting full-length immunoglobulins, and are the host cell system of choice for this particular invention. Similar to expression vectors for other host cells, a eukaryotic cell expression vector will contain the appropriate expression control sequences including promoter (for example, those derived from immunoglobulin genes, metallothionine gene, SV40, Adenovirus, cytomegalovirus, Bovine Papilloma Virus, and the like), enhancers, usually with a leader sequence for directing the expressed polypeptide to the Golgi apparatus for glycosylation and export, the DNA segments of interest (for example, the heavy and light chain encoding sequences and expression control sequences), a termination codon, other necessary processing information sites (such as ribosome binding sites, RNA splice sites, a polyadenylation sequence, and transcriptional terminator sequences), and a selection marker (such as mutant Dhfr, glutamine synthetase (GS), hygromycin, neomycin) (see Kellems, "Gene Amplification in mammalian cells", Marcel Dekker Inc., NY, N.Y., 1993; which is incorporated herein by reference).

There exist a plethora of established and well-known methods for introducing the vectors containing the DNA segments of interest into the host cell, either transiently or stably integrated into the host cell genome. They include, but not limited to, calcium chloride transfection, calcium phosphate treatment, electroporation, lipofection, etc. (See, Maniatis et al., Molecular Cloning: A Laboratory Manual, Cold Spring Harbor Press, 1982; which is incorporated herein by reference). Identification of host cells incorporated with the appropriate expression vector will be achievable typically by first growing cells under selection pressure in accordance with the selectable marker used in the vector, and detection of secreted proteins, for example, the whole antibodies containing two pairs of heavy and light chains, or other immunoglobulin forms of the present invention, by standard procedures such as ELISA and Western analysis. Purification of the expressed immunoglobulin can be purified according to standard procedures of the art, including ammonium sulfate precipitation, affinity columns, column chromatography, gel electrophoresis and the like (see, generally, R. Scopes, "Protein Purification", Springer-Verlag, NY, 1982). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then by used therapeutically (including extracorporeally) or in developing and performing assay procedures, immunofluorescent stainings, and the like (See, generally, Immunological Methods Vols I and II, Lefkovits and Pernis, eds., Academic Press, New York, N.Y., 1979 and 1981).

The antibodies of the present invention will typically find use individually, or in combination with other treatment modalities, in treating diseases susceptible to antibody-based therapy. For example, the immunoglobulins can be used for passive immunization, or the removal of unwanted cells or antigens, such as by complement mediated lysis, all without substantial adverse immune reactions (for example anaphylactic shock) associated with many prior antibodies.

A preferable usage of the antibodies of the present invention will be the treatment of diseases using their naked forms (naked antibodies) at dosages ranging from 50 mg to 400 mg/m$^2$, administered either locally at the lesion site, subcutaneously, intravenously, and intramuscularly, etc. Multiple dosing at different intervals will be performed to achieve optimal therapeutic or diagnostic responses, for example, at weekly intervals, once a week, for four weeks. Usage of the antibodies derived from the present invention can be combined with different treatment modalities, such as chemotherapeutic drugs (for example CHOP, Dox, 5-Fu, . . . etc), radiotherapy, radioimmunotherapy, vaccines, enzymes, toxins/immunotoxins, or other antibodies derived from the present invention or others. The antibodies of the present invention, if specific for the idiotype of an anti-tumor antibody, can be used as tumor vaccines for the elicitation of Ab3 against the tumor antigen. Numerous additional agents, or combinations of agents, well-known to those skilled in the art may also be utilized.

Additionally, the antibodies of the present invention can be utilized in different pharmaceutical compositions. The antibodies can be used in their naked forms, or as conjugated proteins with drugs, radionuclides, toxins, cytokines, soluble factors, hormones, enzymes (for example carboxylesterase, ribonuclease), peptides, antigens (as tumor vaccine), DNA, RNA, or any other effector molecules having a specific therapeutic function with the antibody moiety serving as the targeting agents or delivery vehicles. Moreover, the antibodies or antibody derivatives, such as antibody fragments, single-chain Fv, diabodies, etc. of the present invention can be used as fusion proteins to other functional moieties, such as, antibodies or antibody derivatives of a different invention (for example as bispecific antibodies), toxins, cytokines, soluble factors, hormones, enzymes, peptides, etc. Different combinations of pharmaceutical composition, well-known to those skilled in the art may also be utilized.

FR-patched antibodies of the present invention can also be used for in vitro purposes, for example, as diagnostic tools for the detection of specific antigens, or the like.

The following examples are offered by way of illustration, not by limitation.

EXPERIMENTAL

In designing the amino acid sequence of the FR-patched immunoglobulin chain, the murine variable region sequence (applies to both VH and VL) was compartmentalized into FR1, CDR1, FR2, CDR2, FR3, CDR3, and FR4, according to Kabat's classification (Kabat et al., op. cit.). Selection of the individual FR's for patching was in accordance to the guidelines as described previously.

A human FR1 will be used when it has the highest homology to the parent FR1, preferably 100%, at three or more amino acids immediately adjacent to CDR1.

A human FR2 will be used when it has the highest homology to the parent FR2, preferably 100%, at three or more amino acids at both ends immediately adjacent to the flanking CDR1 and CDR2.

A human FR3 will be used when it has the highest homology to the parent FR3, preferably 100%, at three or more amino acids at both ends immediately adjacent to the flanking CDR2 and CDR3.

A human FR4 will be used when it has the highest homology to the parent FR4, preferably 100%, at three or more amino acids immediately adjacent to CDR3.

In case human FR's with 100% homology at three or more amino acids adjacent to the CDRs cannot be identified, FR's with the closest homology at these positions containing conservatively similar amino acids, such as, gly, ala; val, ile, leu; asp, glu; asn, gln; ser, thr; lys, arg; and phe, tyr; will be selected.

Preferably, human FR's whose amino acids at positions known to be close to, or have interactions with the CDR's/antigen binding site (Chothia and Lesk, op. cit.; Chothia et al., op. cit., and Tramontano et al., op. cit.), either based on computer modeling (see Levy et al., Biochemistry op. cit.; Bruccoleri et al., op. cit.; Chothia et al., op. cit.), crystal structure, published information, or prior experience, which are identical, or conservatively similar to that of the parent FR's will be selected.

In case where a particular human FR satisfying all the above is unavailable, and direct patching results in the loss of affinity or specificity, murine residues considered to have interactions with the antigen binding site, or contribute to the final affinity of the antibody, will be introduced back to the best available FR. Alternatively, the particular FR with no matching human counterpart will be retained and used in its murine composition without modification; the final FR-patched sequence will contain a mixture of human and murine FR's. For the purpose of illustration, two murine anti-B cell antibodies will be FR-patched using the approach as described herein in this invention.

EXAMPLE 1

FR-Patched Anti-CD22 Antibody

Design of Genes for FR-Patched Anti-CD22 Light and Heavy Chain

The heavy and light chain sequence of a murine anti-CD22 antibody, RFB4 (Li et al., Cell Immunol. 118:85, 1989; Mansfield et al., Blood 90:2020-2026, 1997) is used as an example to illustrate the approach of using FR-patching to reduce or eliminate immunogenicity of the re-engineered antibody. The sequences of the heavy (a) and light chain (b) variable region for the murine antibody are shown in FIG. 1.

Patching of the individual FRs for the heavy chain variable region for RFB4 was done as follows:
  a. FR1: the FR1 sequence of the murine VH was compared with the FR1 sequences of human VH from the Kabat's database (Kabat et al., op. cit.). Although human FR1 of the highest sequence homology is preferred, particular emphasis on the sequence closest to the CDR1 was taken. There are three FR1 sequences that are of high homology to the murine FR1. They are, namely, EIK, RF-SJ1, and WAS. The FR1 with the highest overall homology with the five residues closest to the CDR1 identical to the murine parent is EIK, however, there is a missing residue in position 12, which can create potential problems affecting the immunoreactivity of the resultant antibody. The preferred FR1 picked for the patching was therefore from WAS. First, except at position 28, the third closest residue to CDR1, a whole stretch of 11 amino acids next to the CDR1 is identical to the murine parent. In position 28, a serine residue is found instead of an alanine in the murine sequence. Since serine is considered as a hydroxylated version of alanine, the change is conservative. Moreover, residues that are different between the human and murine are relatively similar in characteristics. For example, valine and leucine in position 5, lysine and glutamine at position 13, lysine and arginine at position 19, and alanine and serine at position 28. Therefore, human sequence from WAS was chosen for patching the FR1 of the anti-CD22 antibody (FIG. 2A).
  b. FR2: by the same token and based on the degree of homology, the human WAS sequence is chosen for patching the FR2 of the anti-CD22 antibody (FIG. 2A).
  c. FR3: with the sequences closest to the CDR2, and CDR3 being identical, and the high degree of homology, the human GAL sequence was selected for patching the FR3 of the anti-CD22 antibody (FIG. 2A).
  d. FR4: there are many human FR4 with the sequence closest to the CDR3 being identical, and a high degree of homology to the murine parent. In this example, the human DOB sequence was selected for patching the FR4 of the anti-CD22 antibody (FIG. 2A).

The final design of the FR-patched VH sequence (FIG. 3A) for the anti-CD22 antibody is composed of the human WAS FR1 and FR2, and the GAL FR3 and DOB FR4, replacing the original VH FR's of the anti-CD22 antibody. There is no single mutation or re-introduction of murine FR residues in the final design of the FR-patched sequence.

Using a similar strategy, the sequence design for the FR-patched light chain (VL) was done as follows:
  a. FR1: human JOH was chosen for patching the FR1 of the murine VL. It has a high degree of sequence homology and the stretch of 8 amino acids adjacent to the CDR1 being identical to the parent sequence (FIG. 2B).
  b. FR2: human Vd'CL was chosen for patching the FR2 of the murine VL, for similar reasons. More than 4 identical sequences are adjacent to the CDR1, and CDR2 (FIG. 2B).
  c. FR3: human WES was chosen for patching the FR3 of the murine VL. FR3 has the longest sequence, and the sequence homology between WES and the murine FR3 is high, with the sequences flanking the CDR2 and CDR3 being identical (FIG. 2B).
  d. FR4: human RZ was chosen for patching the FR4 of the murine VL, for similar reasons (FIG. 2B).

The final design of the FR-patched VL sequence (FIG. 3B) for the anti-CD22 antibody is composed of the human JOH FR1, Vd'CL FR2, WES FR3, and RZ FR4, replacing the original VL FR's of the anti-CD22 antibody. Once again, there is no single mutation or re-introduction of murine FR residues in the final design of the FR-patched sequence.

Construction of the FR-Patched Heavy and Light Chain Genes

The designed heavy and light chain variable region sequences of the FR-patched antibody are assembled by a combination of oligonucleotide synthesis and PCR using a variety of published methods (Leung et al., op. cit.; Daugherty et al., op. cit.; DeMartino et al., op. cit.; Jones et al., op. cit.).

To construct the FR-patched heavy chain variable region sequence (SEQ ID no. 1), the full DNA sequence is divided into two halves: the N-terminal half and the C-terminal half. Both are constructed separately by PCR and the complete variable region sequence is formed by joining the N- and C-terminal halves at the KpnI site.

The N-terminal half is constructed as follows: a N-template (SEQ ID no. 3) is a synthetic sense-strand oligonucleotide (111-mer) encoding amino acids 14-50 of the VH region (SEQ ID no. 2). The template is PCR-amplified by two primers:

The 5' Primer (SEQ ID no. 4) is a synthetic sense-strand oligonucleotide (57-mer) encoding amino acids 1-19 of the VH region. The 3' end of the primer overlaps with the 5' end of the template by 18 nucleotides.

The 3' Primer (SEQ ID no. 5) is a synthetic anti-sense-strand oligonucleotide (48-mer) encoding amino acids 43-59. The primer overlaps with the template by 21 nucleotides.

The N-template (SEQ ID no. 3) is PCR-amplified using the 5' and 3' primer set (SEQ ID no. 4 & 5) using standard techniques and procedures.

The C-terminal half is constructed as follows: a C-template (SEQ ID no. 6) is a synthetic sense-strand oligonucleotide (132-mer) encoding amino acids 68-111 of the VH region (SEQ ID no. 2). The template is PCR-amplified by two primers:

The 5' Primer (SEQ ID no. 7) is a synthetic sense-strand oligonucleotide (60-mer) encoding amino acids 55-74 of the VH region. The 3' end of the primer overlaps with the 5' end of the template by 21 nucleotides.

The 3' Primer (SEQ ID no. 8) is a synthetic anti-sense-strand oligonucleotide (58-mer) encoding amino acids 105-123 of the VH region. The primer and the template overlap by 21 nucleotides.

The C-template (SEQ ID no. 6) is PCR-amplified using the 5' and 3' primer set (SEQ ID no. 7 & 8) using standard techniques and procedures.

For the construction of the full-length FR-patched RFB4 VH domain, the N-template (SEQ ID no. 3, 111-mer), C-template (SEQ ID no. 6, 132-mer), and their respective 5'- and 3' primers (SEQ ID no. 4 & 5 for N-template, and SEQ ID no. 7 & 8 for C-template), are synthesized on an automated Applied Biosystem 380B DNA synthesizer (Foster City, Calif.). The oligonucleotides are desalted by passing through a CHROMOSPIN-10™ column (Clonetech, Palo Alto, Calif.). The oligonucleotides are adjusted to a final concentration of 20 μM. One μl of template oligonucleotides at various dilutions (10×, 100×, 1000× and 10000×, etc.) are mixed with 5 μl of their corresponding flanking primers in the presence of 10 μl of 10×PCR Buffer (500 mM KCl, 100 mM Tris.HCl buffer, pH 8.3, 15 mM MgCl2) and 5 units of AMPLITAQ™ DNA polymerase (Perkin Elmer, Applied Biosystems Division, Foster City, Calif.). This reaction mixture is adjusted to a final volume of 100 μl and subjected to 30 cycles of PCR reaction consisting of denaturation at 94° C. for 1 minute, annealing at 50° C. for 1 minutes, and polymerization at 72° C. for 1 minute. The PCR reaction mixtures are analyzed under 2% agarose gel electrophoresis. The highest template dilution that gives rise to sufficiently abundant product of the right size will be chosen for further processing.

Double-stranded PCR-amplified products for the N- and C-templates are gel-purified, restriction-digested with KpnI. The restricted N- and C-double stranded DNA are ligated at the KpnI site, and the ligated products are subjected to another round of PCR amplification using the 5' primer for the N-template (SEQ ID no. 4) and the 3' primer for the C-template (SEQ ID no. 8). The PCR product with a size of ~350 is directly cloned into the TA cloning vector (Invitrogen, San Diego, Calif.). The sequence of the cloned fragment is confirmed by Sanger's method (Sanger et al., PNAS 74:5463-5467, 1977) to be identical to the designed VH sequence. The confirmed sequence is used to replace the VH sequence of a heavy chain expression vector containing an IgH promoter, an Ig enhancer, a human IgG1 constant region genomic sequence, and a selectable marker, gpt. The final heavy chain expression vector is designated as hpRFB4pSMh.

To construct the FR-patched light chain variable region sequence (SEQ ID no. 9), the full length VL variable region sequence is divided into two halves. The N-terminal and C-terminal halves are assembled separately by PCR and joined together via the SpeI site.

The N-terminal half is constructed as follows: a N-template (SEQ ID no. 11) is a synthetic sense-strand oligonucleotide (108-mer) encoding amino acids 11-46 of the VL region (SEQ ID no. 10). The template is PCR-amplified by two primers:

The 5' Primer (SEQ ID no. 12) is a synthetic sense-strand oligonucleotide (51-mer) encoding amino acids 1-17 of the VL region. The 3' end of the primer overlaps with the 5' end of the template by 21 nucleotides.

The 3' Primer (SEQ ID no. 13) is a synthetic anti-sense-strand oligonucleotide (40-mer) encoding amino acids 40-53. The primer overlaps with the template by 18 nucleotides.

The N-template (SEQ ID no. 11) is PCR-amplified using the 5' and 3' primer set (SEQ ID no. 12 & 13) using standard techniques and procedures.

The C-terminal half is constructed as follows: a C-template (SEQ ID no. 14) is a synthetic sense-strand oligonucleotide (120-mer) encoding amino acids 59-98 of the VL region (SEQ ID no. 10). The template is PCR-amplified by two primers:

The 5' Primer (SEQ ID no. 15) is a synthetic sense-strand oligonucleotide (49-mer) encoding amino acids 50-65 of the VL region. The 3' end of the primer overlaps with the 5' end of the template by 21 nucleotides.

The 3' Primer (SEQ ID no. 16) is a synthetic antisense-strand oligonucleotide (48-mer) encoding amino acids 92-107 of the VL region. The primer and the template overlap by 21 nucleotides.

The C-template (SEQ ID no. 14) is PCR-amplified using the 5' and 3' primer set (SEQ ID no. 15 & 16) using standard techniques and procedures.

For the construction of the FR-patched RFB4 VL domain, the N-template (SEQ ID no. 11, 108-mer), C-template (SEQ ID no. 14, 120-mer), and their respective 5'- and 3' primers (SEQ ID no. 12 & 13 for N-template, and SEQ ID no. 15 & 16 for C-template), are synthesized on an automated Applied Biosystem 380B DNA synthesizer. The oligonucleotides are desalted by passing through a CHROMOSPIN-10™ column (Clonetech). The oligonucleotides are adjusted to a final concentration of 20 μM. One μl of template oligonucleotides at various dilutions (10×, 100×, 1000× and 10000×, etc.) are mixed with 5 μl of their corresponding flanking primers in the presence of 10 μl of 10×PCR Buffer (500 mM KCl, 100 mM Tris.HCl buffer, pH 8.3, 15 mM MgCl2) and 5 units of AMPLITAQ™ DNA polymerase (Perkin Elmer). This reaction mixture is adjusted to a final volume of 100 μl and subjected to 30 cycles of PCR reaction consisting of denaturation at 94° C. for 1 minute, annealing at 50° C. for 1 minutes, and polymerization at 72° C. for 1 minute. The PCR reaction mixtures are analyzed under 2% agarose gel electrophoresis. The highest template dilution that gives rise to sufficiently abundant product of the right size will be chosen for further processing.

Double-stranded PCR-amplified products for the N- and C-templates are gel-purified, restriction-digested with SpeI. The restricted N- and C-double stranded DNA are ligated at the SpeI site, and the ligated products are subjected to another round of PCR-amplification using the 5' primer for the N-template (SEQ ID no. 12) and the 3' primer for the C-template (SEQ ID no. 16). The PCR product with a size of ~320 is directly cloned into the TA cloning vector (Invitrogen). The sequence of the cloned fragment is confirmed by Sanger's method (Sanger op. cit.) to be identical to the designed VL sequence. The confirmed sequence is used to replace the VL sequence of a light chain expression vector containing an IgH promoter, an Ig enhancer, a human kappa constant region genomic sequence, and a selectable marker, hyg. The final light chain expression vector is designated as hpRFB4pSMk.

Expression and Affinity of FR-Patched Antibody

The expression plasmids hpRFB4pSMh and hpRFB4pSMk are linearized and co-transfected into mouse Sp2/0 cells. Cells transfected with the plasmids are selected in the presence of mycophenolic acid and/or hygromycin B conferred by the gpt and hyg genes on the plasmids by standard methods. Cells surviving selection are tested for human antibody secretion using ELISA methods. Clones that are identified to be secreting human antibody are expanded for production in 500 ml roller bottles. Antibodies are purified using standard protein A columns. The purified antibody is analyzed in a SDS-PAGE gel under both reducing and non-reducing conditions (Predicted results shown in FIG. 4). The affinity of the FR-patched antibody (hpRFB4) is first evaluated by flow cytometry. Raji cells ($5 \times 10^5$) are incubated with 1 µg of either purified hpRFB4 or chimeric RFB4 (cRFB4) in a final volume of 100 µl of PBS supplemented with 1% FCS and 0.01% (w/v) sodium azide (PBS-FA). cRFB4 differs from hpRFB4 in the variable region sequences which are derived directly from the murine parent without modifications. The mixtures are incubated for 30 minutes at 4° C. and washed three times with PBS to remove unbound antibodies. The binding levels of the antibodies to Raji cells are assessed by the addition of a 20× diluted FITC-labeled, goat anti-human IgG1, Fc fragment-specific antibodies (Jackson ImmunoResearch, West Grove, Pa.) in a final volume of 100 µl in PBS-FA, and incubating for 30 minutes at 4° C. The mixture is washed three times with PBS and fluorescence intensities are measured by a FACSCAN fluorescence-activated cell sorter (Becton Dickinson, Bedford, Mass.) (Predicted results shown in FIG. 5) The predicted results indicate that both antibodies bind well to Raji cells with similar affinity.

To compare the affinity of the antibody before and after re-engineering the VH and VL sequences of RFB4, a competitive binding assay is performed. Fixed amount (10× dilution from stock) of FITC-conjugated RFB4 (Ancell Corporation, Bayport, Minn.) is mixed with varying concentrations of either cRFB4 or hpRFB4. The mixtures are added to Raji cells in a final volume of 100 µl in PBS-FA, and incubated for 30 minutes at 4° C. After washing three times with PBS, the fluorescence intensities of Raji cells bound with the FITC-RFB4 are measured by FASCAN (Becton Dickinson, Bedford, Mass.). The predicted results indicate that FR-patching of the RFB4 sequence does not have significant effects on the affinity of the re-engineered antibody (Predicted results shown in FIG. 6).

EXAMPLE 2

FR-Patched Anti-CD20 Antibody

Design of Genes for FR-Patched Anti-CD20 Light and Heavy Chain.

The heavy and light chain sequence of a murine anti-CD20 antibody, 1F5 (Shan et al. 1999. J Immunol. 162:6589-6595) is used as an example to illustrate the approach of using FR-patching to reduce or eliminate immunogenicity of the re-engineered antibody. The sequences of the heavy and light chain variable region for the murine antibody are shown in FIG. (7).

In designing the amino acid sequence of the FR-patched immunoglobulin for 1F5, the same set of rules as described previously applies. However, there are always situations when no appropriate FR's fulfill all the above-mentioned requirements. The FR-patching approach offers a great degree of flexibility allowing the introduction of murine residues in the problematic FR's, or alternatively, inclusion of the original murine FR's without modifications. The resultant FR-patched antibody will presumably have significantly reduced immunogenicity compared to a murine or chimeric antibody. An anti-CD20 antibody, 1F5, is used as an example for FR-patching to illustrate these points.

Patching of the individual FR's of the 1F5 VH sequence was done as follows:

a. FR1: the FR1 sequence of the murine VH was compared with the FR1 sequences of human VH from the Kabat's database (Kabat et al., op. cit.). Human FR1 of the highest sequence homology is preferred, particularly at the sequences closest to the CDR1. The human FR1 sequence from LS2"CL has close to 80% of sequence homology to that of the murine anti-CD20 antibody, and the 10 residues adjacent to the CDR1 are identical to the murine parent sequence. Therefore, the human FR1 sequence from LS2'CL was chosen for patching the FR1 of the anti-CD20 antibody (FIG. 8A)

b. FR2: the FR2 sequence of the human NEWM was chosen for patching the FR2 sequence of the anti-CD20 antibody. It should be noted that although the third residue of the NEWM FR2 closest to the CDR1 is not identical to that of the murine parent sequence, it is a conserved K to R conversion (FIG. 8A).

c. FR3: human heavy chain FR3 sequences with satisfactorily high sequence homology and identical sequences adjacent to the CDR2 and CDR3 could not be identified. Although the human FR3 from 783C'CL exhibited 78% of sequence homology, the residues flanking the CDR2 are drastically different, despite the differences being conserved. For example, the K, A, and L at positions 57, 58 and 60 (Kabat's numbering, Kabat et al., op. cit.) which are the $1^{st}$, $2^{nd}$, and $4^{th}$ residues closest to the CDR2 are replaced by the conserved human residues R, V and I, respectively. Nevertheless, the high number of changes in proximity to the CDR2, albeit conservative, could result in significant conformational changes at the antigen binding site. Without risking the loss of affinity, and as an illustration on the flexibility of the FR-patching approach, the FR3 would not be patched with any of the human FR's. Instead, the murine FR3 sequence was retained in this particular antibody (FIG. 8A).

d. FR4: there are many human FR4 with the sequence closest to the CDR3 being identical, and a high degree of homology to the murine parent. In this example, the human 4G12'CL sequence was selected for patching the FR4 of the anti-CD20 antibody (FIG. 8A).

The final design of the FR-patched VH sequence (FIG. 9A) for the anti-CD20 antibody is composed of the human LS2'CL FR1, NEWM FR2, murine 1F5 FR3 and 4G12'CL FR4, replacing the original VH FR's of the murine anti-CD20 antibody.

An alternative design will be a patched VH containing the murine CDRs embedded in human LS2'CL FR1, NEWM FR2, 783C'CL FR3, and 4G12'CL FR4 (FIG. 10A). For the purpose of illustration, the construction of the former version will be described below.

Using a similar strategy, the sequence design for the FR-patched light chain was constructed as follows:

a. FR1: human BJ19 was chosen for patching the FR1 of the murine VL. This is the human FR1 sequence with the highest homology to the murine parent (61%). Moreover, some of the human residues that are different from that of the murine are conserved. For example, the E to D, and K to R conversions at positions 18 and 19, respectively, are conserved changes (FIG. 8B).

b. FR2: although there is a human FR2, MOT, that was found to be of high sequence homology (73%) to the murine FR2, the Tryptophan at position 32 (Kabat's numbering, Kabat et al., op. cit.), the $3^{rd}$ residues closest to the CDR2, was replaced by a non-conservative Valine in the MOT FR2 sequence. This replacement potentially might have a significant effect on the final conformation of the antigen binding site. It was therefore determined that the murine FR2 of the VL domain would remain in the design of the FR-patched antibody (FIG. 8B).

c. FR3: human WES was chosen for patching the FR3 of the murine VL. FR3 has the longest sequence, and the sequence homology between WES and the murine FR3 is 71%, with the three human residues flanking the CDR2 and CDR3 being identical to that of the murine (FIG. 8B).

d. FR4: human λ FR4 sequence from NIG-58 was chosen for patching the FR4 of the murine VL, for similar reasons. The sequences are 72% homologous to the stretch of 7 residues adjacent to the CDR3 being identical between the human and murine (FIG. 8B).

The final design of the FR-patched VL sequence (FIG. 9B) for the anti-CD20 antibody is composed of the human BJ19 FR1, murine 1F5 FR2, WES FR3, and NIG-58 FR4, replacing the original VL FR's of the anti-CD20 antibody. An alternative design of FR-patched VL will be composed of the human BJ19 FR1, MOT FR2, WES FR3, and NIG-58 FR4, forming the scaffold supporting the CDR loops (FIG. 10B). For the purpose of illustration in this application, only the construction of the former FR-patched VL will be described below.

Construction of the FR-Patched Heavy and Light Chain Genes

The designed heavy and light chain variable region sequences of the FR-patched antibody are assembled by a combination of oligonucleotide synthesis and PCR using a variety of published methods.

To construct the FR-patched heavy chain variable region sequence (SEQ ID no. 17), the full DNA sequence is divided into two halves. The N-terminal half and the C-terminal half are constructed separately by PCR and the complete variable region sequence is formed by joining the N- and C-terminal halves at the SpeI site.

The N-terminal half is constructed as follows: a N-template (SEQ ID no. 19) is a synthetic sense-strand oligonucleotide (1 14-mer) encoding amino acids 12-49 of the VH region (SEQ ID no. 18). The template is PCR-amplified by two primers:

The 5' Primer (SEQ ID no. 20) is a synthetic sense-strand oligonucleotide (57-mer) encoding amino acids 1-19 of the VH region. The 3' end of the primer overlaps with the 5' end of the template by 24 nucleotides.

The 3' Primer (SEQ ID no. 21) is a synthetic anti-sense-strand oligonucleotide (55-mer) encoding amino acids 43-60. The primer overlaps with the template by 21 nucleotides.

The N-template (SEQ ID no. 19) is PCR-amplified using the 5' and 3' primer set (SEQ ID no. 20 & 21) using standard techniques and procedures.

The C-terminal half is constructed as follows: a C-template (SEQ ID no. 22) is a synthetic sense-strand oligonucleotide (126-mer) encoding amino acids 70-111 of the VH region (SEQ ID no. 18). The template is PCR-amplified by two primers:

The 5' Primer (SEQ ID no. 23) is a synthetic sense-strand oligonucleotide (61-mer) encoding amino acids 57-76 of the VH region. The 3' end of the primer overlaps with the 5' end of the template by 21 nucleotides.

The 3' Primer (SEQ ID no. 24) is a synthetic antisense-strand oligonucleotide (59-mer) encoding amino acids 105-123 of the VH region. The primer and the template overlap by 21 nucleotides.

The C-template (SEQ ID no. 22) is PCR-amplified using the 5' and 3' primer set (SEQ ID no. 23 & 24) using standard techniques and procedures.

For the construction of the FR-patched 1F5 VH domain, the N-template (SEQ ID no. 19, 114-mer), C-template (SEQ ID no. 22, 126-mer), and their respective 5'- and 3' primers (SEQ ID no. 20 & 21 for N-template, and SEQ ID no. 23 & 24 for C-template), are synthesized on an automated Applied Biosystem 380B DNA synthesizer. The oligonucleotides are desalted by passing through a CHROMOSPIN-10™ column (Clonetech). The oligonucleotides are adjusted to a final concentration of 20 μM. One μl of template oligonucleotides at various dilutions (10×, 100×, 1000× and 10000×, etc.) are mixed with 5 μl of their corresponding flanking primers in the presence of 10 μl of 10×PCR Buffer (500 mM KCl, 100 mM Tris.HCl buffer, pH 8.3, 15 mM $MgCl_2$) and 5 units of AMPLITAQ™ DNA polymerase (Perkin Elmer). This reaction mixture is adjusted to a final volume of 100 μl and subjected to 30 cycles of PCR reaction consisting of denaturation at 94° C. for 1 minute, annealing at 50° C. for 1.5 minutes, and polymerization at 72° C. for 1 minute. The PCR reaction mixtures are analyzed under 2% agarose gel electrophoresis. The highest template dilution that gives rise to sufficiently abundant product of the right size will be chosen for further processing.

Double-stranded PCR-amplified products for the N- and C-templates are gel-purified, restriction-digested with KpnI site. The N- and C-double stranded DNA are ligated at the SpeI site, and the ligated products are subjected to another round of PCR amplification using the 5' primer for the N-template (SEQ ID no. 19) and the 3' primer for the C-template (SEQ ID no. 22). The PCR product with a size of ~350 is directly cloned into the TA cloning vector (Invitrogen). The sequence of the cloned fragment is confirmed by Sanger's method (Sanger et al. op. cit.) to be identical to the designed VH sequence. The confirmed sequence is used to replace the VH sequence of a heavy chain expression vector containing an IgH promoter, an Ig enhancer, a human IgG1 constant region genomic sequence, and a selectable marker, gpt. The final heavy chain expression vector is designated as hp1F5pSMh.

To construct the FR-patched light chain variable region sequence (SEQ ID no. 25), the full length VL variable region sequence is divided into two halves. The N-terminal and C-terminal halves are assembled separately by PCR and joined together via the BspEI site.

The N-terminal half is constructed as follows: a N-template (SEQ ID no. 27) is a synthetic sense-strand oligonucleotide (129-mer) encoding amino acids 9-51 of the VL region (SEQ ID no. 26). The template is PCR-amplified by two primers:

The 5' Primer (SEQ ID no. 28) is a synthetic sense-strand oligonucleotide (45-mer) encoding amino acids 1-15 of the VH region. The 3' end of the primer overlaps with the 5' end of the template by 21 nucleotides.

The 3' Primer (SEQ ID no. 29) is a synthetic anti-sense-strand oligonucleotide (40-mer) encoding amino acids 45-57. The primer overlaps with the template by 21 nucleotides.

The N-template (SEQ ID no. 27) is PCR-amplified using the 5' and 3' primer set (SEQ ID no. 28 & 29) using standard techniques and procedures.

The C-terminal half is constructed as follows: a C-template (SEQ ID no. 30) is a synthetic sense-strand oligonucleotide (120-mer) encoding amino acids 61-100 of the VH region (SEQ ID no. 26). The template is PCR-amplified by two primers:

The 5' Primer (SEQ ID no. 31) is a synthetic sense-strand oligonucleotide (43-mer) encoding amino acids 54-67 of the VH region. The 3' end of the primer overlaps with the 5' end of the template by 21 nucleotides.

The 3' Primer (SEQ ID no. 32) is a synthetic antisense-strand oligonucleotide (42-mer) encoding amino acids 94-107 of the VH region. The primer and the template overlap by 21 nucleotides.

The C-template (SEQ ID no. 30) is PCR-amplified using the 5' and 3' primer set (SEQ ID no. 31 & 32) using standard techniques and procedures.

For the construction of the FR-patched 1F5 VL domain, the N-template (SEQ ID no. 27, 129-mer), C-template (SEQ ID no. 30, 120-mer), and their respective 5'- and 3' primers (SEQ ID no. 28 & 29 for N-template, and SEQ ID no. 31 & 32 for C-template), are synthesized on an automated Applied Biosystem 380B DNA synthesizer. The oligonucleotides are desalted by passing through a CHROMOSPIN-10™ column (Clonetech). The oligonucleotides are adjusted to a final concentration of 20 μM. One μl of template oligonucleotides at various dilutions (10×, 100×, 1000× and 10000×, etc.) are mixed with 5 μl of their corresponding flanking primers in the presence of 10 μl of 10×PCR Buffer (500 mM KCl, 100 mM Tris.HCl buffer, pH 8.3, 15 mM $MgCl_2$) and 5 units of AMPLITAQ™ DNA polymerase (Perkin Elmer). This reaction mixture is adjusted to a final volume of 100 μl and subjected to 30 cycles of PCR reaction consisting of denaturation at 94° C. for 1 minute, annealing at 50° C. for 1.5 minutes, and polymerization at 72° C. for 1 minute. The PCR reaction mixtures are analyzed under 2% agarose gel electrophoresis. The highest template dilution that gives rise to sufficiently abundant product of the right size will be chosen for further processing.

Double-stranded PCR-amplified products for the N- and C-templates are gel-purified, restriction-digested with SpeI site. The N- and C-double stranded DNA are ligated at the BspEI site, and amplified using the 5' primer for the N-template (SEQ ID no. 12) and the 3' primer for the C-template (SEQ ID no. 16). The PCR product with a size of ~320 is directly cloned into the TA cloning vector (Invitrogen). The sequence of the cloned fragment is confirmed by Sanger's method (Sanger et al., op. cit.) to be identical to the designed VL sequence. The confirmed sequence is used to replace the VL sequence of a light chain expression vector containing an IgH promoter, an Ig enhancer, a human kappa constant region genomic sequence, and a selectable marker, hyg. The final light chain expression vector is designated as hp1F5pSMk.

SEQUENCE LISTING

```
<160> NUMBER OF SEQ ID NOS: 32

<210> SEQ ID NO 1
<211> LENGTH: 369
<212> TYPE: DNA
<213> ORGANISM: Artificial Sequence
<220> FEATURE:
<223> OTHER INFORMATION: FR-patched heavy chaim variable region
      sequence (Full DNA Sequence) formed by joining the N- and C-
      terminal (SEQ 3 and 6) halves at the KpeI site.
<220> FEATURE:
<221> NAME/KEY: V_region
<222> LOCATION: (1)..(369)
<223> OTHER INFORMATION:

<400> SEQUENCE: 1
gaagtgcagc tgctggagtc tgggggaggc ttagtgcagc ctggagggtc cctgaggctc         60
tcctgtgcag cctctggatt ctccttcagt atctatgaca tgtcttgggt tcgccaggca        120
ccgggaaagg ggctggagtg ggtcgcatac attagtagtg gtggtggtac cacctactat        180
ccagacactg tgaagggccg attcaccatc tccagagaca tgccaagaa  ctccctgtac        240 ctgcaaatga acagtctgag ggtggaggac acagccttat attactgtgc aagacatagt        300
```

```
ggctacggta gtagctacgg ggttttgttt gcttactggg gccaagggac tctggtcact        360
gtctcttca                                                                369
```

<210> SEQ ID NO 2
<211> LENGTH: 123
<212> TYPE: PRT
<213> ORGANISM: Chimaera sp.

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Thr Thr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Arg His Ser Gly Tyr Gly Ser Tyr Gly Val Leu Phe Ala Tyr
            100                 105                 110

Trp Gly Gln Gly Thr Leu Val Thr Val Ser Ser
        115                 120
```

<210> SEQ ID NO 3
<211> LENGTH: 111
<212> TYPE: DNA
<213> ORGANISM: Artificial Sequence
<220> FEATURE:
<223> OTHER INFORMATION: N-template is a synthetic sense-strand
      oligonucleotide encoding a mino acide 14-50 of the VH region (SEQ
      ID No. 2). The template is PCR-amplified by two primers (SEQ ID
      No. 4 and 5)
<220> FEATURE:
<221> NAME/KEY: V_region
<222> LOCATION: (1)..(111)
<223> OTHER INFORMATION:

<400> SEQUENCE: 3

```
cctggagggt ccctgaggct ctcctgtgca gcctctggat tctccttcag tatctatgac        60
atgtcttggg ttcgccaggc accgggaaag gggctggagt gggtcgcata c                111
```

<210> SEQ ID NO 4
<211> LENGTH: 57
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 1-19 of the VH region (SEQ ID
      No. 2). The 3' end of the primer overlaps with the 5'end of the
      template by 18 nucleotides
      .
<220> FEATURE:
<221> NAME/KEY: primer_bind
<222> LOCATION: (1)..(57)
<223> OTHER INFORMATION:

<400> SEQUENCE: 4

```
gaagtgcagc tgctggagtc tgggggaggc ttagtgcagc ctggagggtc cctgagg          57
```

<210> SEQ ID NO 5
<211> LENGTH: 48
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 43-59 of the VH region(SEQ ID
      No. 2). The primer overlaps with the template by 21 nucleotides.

<220> FEATURE:
<221> NAME/KEY: primer_bind
<222> LOCATION: (1)..(48)
<223> OTHER INFORMATION:

<400> SEQUENCE: 5
gtaggtggta ccaccaccac tactaatgta tgcgacccac tccagccc                48

<210> SEQ ID NO 6
<211> LENGTH: 132
<212> TYPE: DNA
<213> ORGANISM: Artificial Sequence
<220> FEATURE:
<223> OTHER INFORMATION: C-terminal is a synthetic sense-strand
      oligonucleotide encoding amino acid 68-111 of the VH region (SEQ
      ID No 2) The template is PCR-amplified by two primers (SEQ ID
      No 7 and 8)
<220> FEATURE:
<221> NAME/KEY: V_region
<222> LOCATION: (1)..(132)
<223> OTHER INFORMATION:

<400> SEQUENCE: 6
ttcaccatct ccagagacaa tgccaagaac tccctgtacc tgcaaatgaa cagtctgagg       60
gtggaggaca cagccttata ttactgtgca agacatagtg gctacggtag tagctacggg      120
gttttgtttg ct                                                          132

<210> SEQ ID NO 7
<211> LENGTH: 60
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 55-74 of the VH region (SEQ
      ID No 2). The 3' end of the primer overlaps with the 5'end of
      the template by 21 nucleotides
      .
<220> FEATURE:
<221> NAME/KEY: primer_bind
<222> LOCATION: (1)..(60)
<223> OTHER INFORMATION:

<400> SEQUENCE: 7
ggtggtacca cctactatcc agacactgtg aagggccgat tcaccatctc cagagacaat       60

<210> SEQ ID NO 8
<211> LENGTH: 57
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 105-123 of the VH region (SEQ
      ID No 2). The primer and the template overlaps by 21 nucleotides.
<220> FEATURE:
<221> NAME/KEY: primer_bind
<222> LOCATION: (1)..(57)
<223> OTHER INFORMATION:

<400> SEQUENCE: 8
tgaagagaca gtgaccagag tcccttggcc ccagtaagca acaaaaccc cgtagct           57

<210> SEQ ID NO 9
<211> LENGTH: 321
<212> TYPE: DNA
<213> ORGANISM: Artificial Sequence
<220> FEATURE:
<223> OTHER INFORMATION: FR-patched light chaim variable region
sequence formed by joining the N- and C- terminal (SEQ 11 and 14)
halves at the KpeI site.
<220> FEATURE:
<221> NAME/KEY: V_region
<222> LOCATION: (1)..(321)
<223> OTHER INFORMATION:

<400> SEQUENCE: 9

```
gatatccaga tgacccagtc tccatcctcc ctgtctgcct ctgtgggaga cagagtcacc      60
attagttgca gggcaagtca ggacattagc aattatttaa actggtatca gcagaaacca     120
ggtaaggctc cgaaactcct gatctactac actagtatat tacactcagg agtcccatca     180
aggttcagtg gcagtgggtc tggaacagaa tttactctca ccattagctc cctgcagcca     240
gaagattttg ccacttactt ttgccaacag gtaatacgc ttccgtggac gttcggtgga     300
ggcaccaagg tggaaatcaa a                                               321
```

<210> SEQ ID NO 10
<211> LENGTH: 107
<212> TYPE: PRT
<213> ORGANISM: Chimaera sp.

<400> SEQUENCE: 10

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys
            100                 105
```

<210> SEQ ID NO 11
<211> LENGTH: 108
<212> TYPE: DNA
<213> ORGANISM: Artificial Sequence
<220> FEATURE:
<223> OTHER INFORMATION: N-template is a synthetic sense-strand
oligonucleotide encoding amino acid 11-46 of the VL region (SEQ
ID No. 10). The template is PCR-amplified by two primers (SEQ
ID No. 12 and 13)
<220> FEATURE:
<221> NAME/KEY: V_region
<222> LOCATION: (1)..(108)
<223> OTHER INFORMATION:

<400> SEQUENCE: 11

```
ctgtctgcct ctgtgggaga cagagtcacc attagttgca gggcaagtca ggacattagc      60
aattatttaa actggtatca gcagaaacca ggtaaggctc cgaaactc                  108
```

```
<210> SEQ ID NO 12
<211> LENGTH: 51
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 1-17 of the VH region (SEQ ID
      No 10). The 3' end of the primer overlaps with the 5'end of the
      template by 21 nucleotides
      .
<220> FEATURE:
<221> NAME/KEY: primer_bind
<222> LOCATION: (1)..(51)
<223> OTHER INFORMATION:

<400> SEQUENCE: 12
gatatccaga tgacccagtc tccatcctcc ctgtctgcct ctgtgggaga c        51

<210> SEQ ID NO 13
<211> LENGTH: 40
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 40-53. The primer and the
      template overlaps by 18 nucleotides.
<220> FEATURE:
<221> NAME/KEY: primer_bind
<222> LOCATION: (1)..(40)
<223> OTHER INFORMATION:

<400> SEQUENCE: 13
atatactagt gtagtagatc aggagtttcg gagccttacc                      40

<210> SEQ ID NO 14
<211> LENGTH: 120
<212> TYPE: DNA
<213> ORGANISM: Artificial Sequence
<220> FEATURE:
<223> OTHER INFORMATION: C-terminal is a synthetic sense-strand
      oligonucleotide encoding amino acid 59-98 of the VH region (SEQ
      ID No 10) The template is PCR-amplified by tow primers (SEQ ID No
      15 and 16)
<220> FEATURE:
<221> NAME/KEY: V_region
<222> LOCATION: (1)..(120)
<223> OTHER INFORMATION:

<400> SEQUENCE: 14
ccatcaaggt tcagtggcag tgggtctgga acagaattta ctctcaccat tagctccctg   60
cagccagaag attttgccac ttactttgc caacagggta tacgcttcc gtggacgttc    120

<210> SEQ ID NO 15
<211> LENGTH: 49
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 50-65 of the VH region (SEQ
      ID No. 10). The 3' end of the primer overlaps with the 5'end of
      the template by 21 nucleotides
<220> FEATURE:
<221> NAME/KEY: primer_bind
<222> LOCATION: (1)..(49)
<223> OTHER INFORMATION:

<400> SEQUENCE: 15
ctacactagt atattacact caggagtccc atcaaggttc agtggcagt             49

<210> SEQ ID NO 16
```

```
<211> LENGTH: 48
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 92-107 of the VH region (SEQ
      ID No 10). The primer and the template overlaps by 21
      nucleotides.
<220> FEATURE:
<221> NAME/KEY: primer_bind
<222> LOCATION: (1)..(48)
<223> OTHER INFORMATION:

<400> SEQUENCE: 16
tttgatttcc accttggtgc ctccaccgaa cgtccacgga agcgtatt                48

<210> SEQ ID NO 17
<211> LENGTH: 371
<212> TYPE: DNA
<213> ORGANISM: Artificial Sequence
<220> FEATURE:
<223> OTHER INFORMATION: FR-patched heavy chaim variable region
      sequence (Full DNA Sequence) formed by joining the N- and C-
      terminal (SEQ 19 and 22) halves at the KpeI site.
<220> FEATURE:
<221> NAME/KEY: V_region
<222> LOCATION: (1)..(371)
<223> OTHER INFORMATION:

<400> SEQUENCE: 17
caggtgcaac tggtggcttc cggggctgag gtaaataagc ctggggcctc agtgaaggtc    60
tcctgcaagg cttctggcta cacatttacc agttacaata tgcactgggt acggcagcct   120
cctggaaggg gcctggaatg gattggagct atttatccag gaaatggtga tactagttac   180
aatcagaaat tcaagggcaa ggccacattg actgcagaca aatcctccag cacagcctac   240
atgcagctca gcagtctgac atctgaggac tctgcggtct attactgtgc aagatcgcac   300
tacggtagta actacgtaga ctactttgac tactggggcc aaggcaccac tgttacagtc   360
tcctctgatc a                                                        371

<210> SEQ ID NO 18
<211> LENGTH: 123
<212> TYPE: PRT
<213> ORGANISM: Chimaera sp.

<400> SEQUENCE: 18

Gln Val Gln Leu Val Ala Ser Gly Ala Glu Val Asn Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Thr Val Thr Val Ser Ser Asp
        115                 120
```

<210> SEQ ID NO 19
<211> LENGTH: 114
<212> TYPE: DNA
<213> ORGANISM: Artificial Sequence
<220> FEATURE:
<223> OTHER INFORMATION: N-template is a synthetic sense-strand oligonucleotide encoding amino acids 12-49 of the VH region (SEQ ID No. 18). The template is PCR-amplified by two primers (SEQ ID No. 20 and 21)
<220> FEATURE:
<221> NAME/KEY: V_region
<222> LOCATION: (1)..(114)
<223> OTHER INFORMATION:

<400> SEQUENCE: 19
aataagcctg gggcctcagt gaaggtctcc tgcaaggctt ctggctacac atttaccagt      60
tacaatatgc actgggtacg gcagcctcct ggaagggggcc tggaatggat tgga          114

<210> SEQ ID NO 20
<211> LENGTH: 57
<212> TYPE: DNA
<213> ORGANISM: Artificial Sequence
<220> FEATURE:
<223> OTHER INFORMATION: 5' Primer is a synthetic sense-strand oligonucleotide encoding amino acid 1-19 of the VH region (SEQ ID No 18). The 3' end of the primer overlaps with the 5'end of the template by 24 nucleotides
.
<220> FEATURE:
<221> NAME/KEY: primer_bind
<222> LOCATION: (1)..(57)
<223> OTHER INFORMATION:

<400> SEQUENCE: 20
caggtgcaac tggtggcttc cggggctgag gtaaataagc ctggggcctc agtgaag        57

<210> SEQ ID NO 21
<211> LENGTH: 55
<212> TYPE: DNA
<213> ORGANISM: Artificial Sequence
<220> FEATURE:
<223> OTHER INFORMATION: 3' Primer is a synthetic anti-sense-strand oligonucleotide encoding amino acid 43-60 of the VH region (SEQ ID No 18). The primer and the template overlaps by 21 nucleotides.
<220> FEATURE:
<221> NAME/KEY: primer_bind
<222> LOCATION: (1)..(55)
<223> OTHER INFORMATION:

<400> SEQUENCE: 21
tgtaactagt atcaccattt cctggataaa tagctccaat ccattccagg cccct          55

<210> SEQ ID NO 22
<211> LENGTH: 126
<212> TYPE: DNA
<213> ORGANISM: Artificial Sequence
<220> FEATURE:
<223> OTHER INFORMATION: C-terminal is a synthetic sense-strand oligonucleotide encoding amino acid 70-111 of the VH region (SEQ ID No 18) The template is PCR-amplified by tow primers (SEQ ID No 23 and 24)
<220> FEATURE:
<221> NAME/KEY: V_region
<222> LOCATION: (1)..(126)
<223> OTHER INFORMATION:

<400> SEQUENCE: 22
ttgactgcag acaaatcctc cagcacagcc tacatgcagc tcagcagtct gacatctgag     60

```
gactctgcgg tctattactg tgcaagatcg cactacggta gtaactacgt agactacttt    120
gactac                                                               126
```

<210> SEQ ID NO 23
<211> LENGTH: 61
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 57-76 of the VH region (SEQ
      ID No 18). The 3' end of the primer overlaps with the 5'end of
      the template by 21 nucleotides.
<220> FEATURE:
<221> NAME/KEY: primer_bind
<222> LOCATION: (1)..(61)
<223> OTHER INFORMATION:

<400> SEQUENCE: 23

```
tgatactagt tacaatcaga aattcaaggg caaggccaca ttgactgcag acaaatcctc    60
c                                                                    61
```

<210> SEQ ID NO 24
<211> LENGTH: 59
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 105-123 of the VH region
      (SEQ ID No 18). The primer and the template overlaps by 21
      nucleotides.
<220> FEATURE:
<221> NAME/KEY: primer_bind
<222> LOCATION: (1)..(59)
<223> OTHER INFORMATION:

<400> SEQUENCE: 24

```
tgatcagagg agactgtaac agtggtgcct tggccccagt agtcaaagta gtctacgta     59
```

<210> SEQ ID NO 25
<211> LENGTH: 321
<212> TYPE: DNA
<213> ORGANISM: Artificial Sequence
<220> FEATURE:
<223> OTHER INFORMATION: FR-patched light chaim variable region
      sequence (Full DNA Sequence) formed by joining the N- and C-
      terminal (SEQ 27 and 30) halves at the BspEI site.
<220> FEATURE:
<221> NAME/KEY: V_region
<222> LOCATION: (1)..(321)
<223> OTHER INFORMATION:

<400> SEQUENCE: 25

```
gatattcaac tcacacagtc tccatcaagt ctttctgcat ctgtggggga cagagtcaca    60
attacttgca gggccagctc aagtttaagt tcatgcact ggtaccagca gaagccagga    120
tcctccccca aaccctggat ttatgccaca tccaacctgg cttccggagt ccctagtcgc   180
ttcagtggca gtgggtctgg gaccgagttc actctcacaa tcagcagttt gcagcctgaa   240
gatttcgcca cttatttctg ccatcagtgg agtagtaacc cgctcacgtt cggtgctggg   300
accaagctga ccgttctacg g                                             321
```

<210> SEQ ID NO 26
<211> LENGTH: 107
<212> TYPE: PRT
<213> ORGANISM: Chimaera sp.

<400> SEQUENCE: 26

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Leu Ser Phe Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Phe Cys His Gln Trp Ser Ser Asn Pro Leu Thr
                85                  90                  95

Phe Gly Ala Gly Thr Lys Leu Thr Val Leu Arg
            100                 105
```

<210> SEQ ID NO 27
<211> LENGTH: 129
<212> TYPE: DNA
<213> ORGANISM: Artificial Sequence
<220> FEATURE:
<223> OTHER INFORMATION: N-template is a synthetic sense-strand
      oligonucleotide encoding amino acide 9-51 of the VL region (SEQ
      ID No. 26). The template is PCR-amplified by two primers (SEQ ID
      No. 28 and 29)
<220> FEATURE:
<221> NAME/KEY: V_region
<222> LOCATION: (1)..(129)
<223> OTHER INFORMATION:

<400> SEQUENCE: 27
tcaagtcttt ctgcatctgt gggggacaga gtcacaatta cttgcagggc cagctcaagt    60
ttaagtttca tgcactggta ccagcagaag ccaggatcct cccccaaacc ctggatttat   120
gccacatcc                                                            129

<210> SEQ ID NO 28
<211> LENGTH: 45
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 1-15 of the VH region (SEQ ID
      No 26). The 3' end of the primer overlaps with the 5'end of the
      template by 21 nucleotides
      .
<220> FEATURE:
<221> NAME/KEY: primer_bind
<222> LOCATION: (1)..(45)
<223> OTHER INFORMATION:

<400> SEQUENCE: 28
gatattcaac tcacacagtc tccatcaagt ctttctgcat ctgtg                     45

<210> SEQ ID NO 29
<211> LENGTH: 40
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 45-57. The primer and the
      template overlaps by 21 nucleotides.
<220> FEATURE:
<221> NAME/KEY: primer_bind
<222> LOCATION: (1)..(40)
<223> OTHER INFORMATION:

-continued

```
<400> SEQUENCE: 29
ggactccgga agccaggttg gatgtggcat aaatccaggg                              40

<210> SEQ ID NO 30
<211> LENGTH: 120
<212> TYPE: DNA
<213> ORGANISM: Artificial Sequence
<220> FEATURE:
<223> OTHER INFORMATION: C-terminal is a synthetic sense-strand
      oligonucleotide encoding amino acid 61-100 of the VH region (SEQ
      ID No 26) The template is PCR-amplified by tow primers (SEQ ID
      No 31 and 32)
<220> FEATURE:
<221> NAME/KEY: V_region
<222> LOCATION: (1)..(120)
<223> OTHER INFORMATION:

<400> SEQUENCE: 30
ttcagtggca gtgggtctgg gaccgagttc actctcacaa tcagcagttt gcagcctgaa        60
gatttcgcca cttatttctg ccatcagtgg agtagtaacc cgctcacgtt cggtgctggg       120

<210> SEQ ID NO 31
<211> LENGTH: 43
<212> TYPE: DNA
<213> ORGANISM: Artificial Sequence
<220> FEATURE:
<223> OTHER INFORMATION: 5' Primer is a synthetic sense-strand
      oligonucleotide encoding amino acid 54-67 of the VH region (SEQ
      ID No 18). The 3' end of the primer overlaps with the 5'end of
      the template by 21 nucleotides.
<220> FEATURE:
<221> NAME/KEY: primer_bind
<222> LOCATION: (1)..(43)
<223> OTHER INFORMATION:

<400> SEQUENCE: 31
ggcttccgga gtccctagtc gcttcagtgg cagtgggtct ggg                          43

<210> SEQ ID NO 32
<211> LENGTH: 42
<212> TYPE: DNA
<213> ORGANISM: Artificial Sequence
<220> FEATURE:
<223> OTHER INFORMATION: 3' Primer is a synthetic anti-sense-strand
      oligonucleotide encoding amino acid 94-107 of the VH region (SEQ
      ID No 26). The primer and the template overlaps by 21
      nucleotides.
<220> FEATURE:
<221> NAME/KEY: primer_bind
<222> LOCATION: (1)..(42)
<223> OTHER INFORMATION:

<400> SEQUENCE: 32
ccgtagaacg gtcagcttgg tcccagcacc gaacgtgagc gg                           42
```

What is claimed is:

1. A method for producing an immunoglobulin containing 3 heavy chain and 3 light chain complementary determining regions from the mouse 1F5 immunoglobulin and framework sequences from human immunoglobulins comprising the steps of:

a. dividing the framework sequences from the 1F5 immunoglobulin into compartmentalized sub-regions of FR1, FR2, FR3, and FR4 according to the classification of the Kabat Database;

b. comparing the individual sub-region framework sequences to corresponding sequences in a collection of human immunoglobulin chains;

c. selecting, from the collection, the appropriate human framework sequences to replace the original framework sequences of the FR1, FR2, FR3 and FR4 sub-regions of the 1F5 immunoglobulin, wherein the resulting immunoglobulin comprises a heavy chain variable region having the amino acid sequence of SEQ ID NO: 70, and a light chain variable region having the amino acid sequence of SEQ ID NO: 71;

d. assembling the framework sequences selected in step c;
e. subcloning the assembled framework sequences of step d into heavy and light chain expression vectors containing appropriate immunoglobulin constant heavy and light chain nucleotide sequences;
f. co-transfecting mouse Sp2/0 cells with the expression vectors of step e;
g. culturing the mouse Sp2/0 cells of step f under conditions permitting expression and secretion of immunoglobulin.

2. The method of claim 1 wherein the immunoglobulin constant heavy and light chain nucleotide sequences are human IgG1 and human kappa constant region sequences, respectively.

* * * * *